US011511063B2

(12) United States Patent
Buschke et al.

(10) Patent No.: US 11,511,063 B2
(45) Date of Patent: Nov. 29, 2022

(54) VENTILATOR AND PROCESS FOR THE AUTOMATED VENTILATION OF A PATIENT

(71) Applicant: Drägerwerk AG & Co. KGaA, Lübeck (DE)

(72) Inventors: Wilfried Buschke, Lübeck (DE); Christoph Hörmann, Mank (AT); Stefan Mersmann, Lübeck (DE)

(73) Assignee: DRÄGER WERK AG & CO. KGAA, Lübeck (DE)

( * ) Notice: Subject to any disclaimer, the term of this patent is extended or adjusted under 35 U.S.C. 154(b) by 622 days.

(21) Appl. No.: 15/780,409

(22) PCT Filed: Nov. 21, 2016

(86) PCT No.: PCT/EP2016/001953
§ 371 (c)(1),
(2) Date: May 31, 2018

(87) PCT Pub. No.: WO2017/092851
PCT Pub. Date: Jun. 8, 2017

(65) Prior Publication Data
US 2018/0344959 A1    Dec. 6, 2018

(30) Foreign Application Priority Data
Dec. 2, 2015    (DE) .................... 10 2015 015 439.7

(51) Int. Cl.
*A61M 16/00*    (2006.01)
*A61M 16/10*    (2006.01)
(Continued)

(52) U.S. Cl.
CPC ...... *A61M 16/024* (2017.08); *A61M 16/0003* (2014.02); *A61M 16/0051* (2013.01);
(Continued)

(58) Field of Classification Search
CPC .............. A61M 16/00; A61M 16/0003; A61M 16/0051; A61M 16/01; A61M 16/021;
(Continued)

(56) References Cited

U.S. PATENT DOCUMENTS 4,838,257 A * 6/1989 Hatch ................. A61M 16/204
128/204.18
5,752,509 A * 5/1998 Lachmann .......... A61M 16/024
128/203.12
(Continued)

FOREIGN PATENT DOCUMENTS

CN        1074620 A      7/1993
CN      101448539 A      6/2009
(Continued)

OTHER PUBLICATIONS

"Modes of ventilation in Intensive Care," Karin Deden, Dräger Medical GmbH.
(Continued)

*Primary Examiner* — Colin W Stuart
(74) *Attorney, Agent, or Firm* — McGlew and Tuttle, P.C.

(57) ABSTRACT

A ventilator, for the automated ventilation of a patient, includes a breathing gas delivery unit, at least one volume flow sensor for detecting a volume flow of the breathing gas, at least one breathing gas sensor for detecting a carbon dioxide concentration in the breathing gas, at least one pressure sensor for detecting a pressure of the breathing gas, as well as at least one computer. The computer is configured to actuate the breathing gas delivery unit as a function of the detected pressure and of a preset desired pressure value. The computer is further configured to perform an adaptation of the desired pressure value and an adaptation of a ventilation rate as a function of the detected volume flow and as a function of the detected carbon dioxide concentration.

16 Claims, 17 Drawing Sheets

(51) Int. Cl.
  *A61M 16/01* (2006.01)
  *A61M 16/08* (2006.01)
  *A61M 16/20* (2006.01)
  *A61M 16/22* (2006.01)
(52) U.S. Cl.
  CPC .......... *A61M 16/01* (2013.01); *A61M 16/021* (2017.08); *A61M 16/022* (2017.08); *A61M 16/0891* (2014.02); *A61M 16/104* (2013.01); *A61M 16/0072* (2013.01); *A61M 16/085* (2014.02); *A61M 16/208* (2013.01); *A61M 16/22* (2013.01); *A61M 2016/003* (2013.01); *A61M 2016/0027* (2013.01); *A61M 2016/0039* (2013.01); *A61M 2016/103* (2013.01); *A61M 2205/3303* (2013.01); *A61M 2205/50* (2013.01); *A61M 2230/42* (2013.01); *A61M 2230/432* (2013.01)
(58) Field of Classification Search
  CPC .. A61M 16/022; A61M 16/024; A61M 16/10; A61M 2016/0015; A61M 2016/0027; A61M 2016/003; A61M 2016/103; A61M 2016/102; A61M 2016/0039; A61M 2202/0225; A61M 2205/33; A61M 2205/3327; A61M 2205/3331; A61M 2205/3334; A61M 2230/40; A61M 2230/432; A61M 2230/43
  See application file for complete search history.

(56) References Cited

U.S. PATENT DOCUMENTS

| | | | |
|---|---|---|---|
| 2007/0221224 A1 | 9/2007 | Pittman et al. | |
| 2009/0320836 A1* | 12/2009 | Baker, Jr. | A61M 16/125 128/203.14 |
| 2010/0300445 A1 | 12/2010 | Chatburn et al. | |
| 2011/0041850 A1* | 2/2011 | Vandine | A61B 5/7246 128/204.23 |
| 2013/0047989 A1* | 2/2013 | Vandine | A61M 16/026 128/204.23 |
| 2013/0074844 A1* | 3/2013 | Kimm | A61M 16/024 128/204.23 |
| 2013/0133656 A1* | 5/2013 | Nightingale | A61B 5/4809 128/204.23 |
| 2013/0255687 A1* | 10/2013 | Rahlf | A61M 16/0891 128/204.26 |
| 2014/0311491 A1* | 10/2014 | Klein | A61M 16/12 128/204.22 |
| 2015/0114395 A1 | 4/2015 | Heinonen et al. | |
| 2016/0001001 A1* | 1/2016 | Wruck | A61M 5/1723 128/204.23 |
| 2016/0180044 A1* | 6/2016 | Delisle | G16H 40/67 705/3 |

FOREIGN PATENT DOCUMENTS

| | | |
|---|---|---|
| CN | 103813823 A | 5/2014 |
| CN | 103 893 866 A | 7/2014 |
| DE | 10 2011 106406 A1 | 1/2013 |
| DE | 10 2012 024672 A1 | 6/2014 |
| JP | H09-24099 A | 1/1997 |
| JP | 2001-517960 A | 10/2001 |
| JP | 2011-045592 A | 3/2011 |
| WO | 2007085108 A1 | 8/2007 |

OTHER PUBLICATIONS

"Zeus Infinity Empowered" manual, Dräger Medical AG & Co. KG, 1st edition, Feb. 2009.

* cited by examiner

T2

| Level of ventilation | | | |
|---|---|---|---|
| normal ventilated | Lung mechanic | | |
| ZoRC Parameter | normal | obstructive | restrictive |
| etCO$_2$U1 [mmHg] | 35 | 45 | 35 |
| etCO$_2$O1 [mmHg] | 45 | 55 | 45 |
| Level of ventilation | | | |
| mild hyperventilated | Lung mechanic | | |
| ZoRC Parameter | normal | obstructive | restrictive |
| etCO$_2$U1 [mmHg] | 30 | 40 | 30 |
| etCO$_2$O2 [mmHg] | 40 | 50 | 40 |
| | Lung mechanic | | |
| ZoRC Parameter | normal | obstructive | restrictive |
| VTU1 [ml/kg] | 7 | 3 | 2 |
| VTO1 [ml/kg] | 10 | 10 | 6 |

| Level of ventilation | | | |
|---|---|---|---|
| normal ventilated | Lung mechanic | | |
| ZoRC Parameter | normal | obstructive | restrictive |
| etCO$_2$U1 [mmHg] | 35 | 50 | 35 |
| etCO$_2$O1 [mmHg] | 45 | 60 | 45 |
| Level of ventilation | | | |
| mild hyperventilated | Lung mechanic | | |
| ZoRC Parameter | normal | obstructive | restrictive |
| etCO$_2$U1 [mmHg] | n/a | n/a | n/a |
| etCO$_2$O1 [mmHg] | n/a | n/a | n/a |
| | Lung mechanic | | |
| ZoRC Parameter | normal | obstructive | restrictive |
| VTU1 [ml/kg] | 4 | 4 | 2 |
| VTO1 [ml/kg] | 8 | 8 | 5 |

FIG. 12b

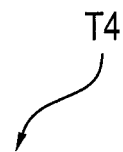

| | Level of ventilation | | |
|---|---|---|---|
| normal ventilated | Lung mechanic | | |
| ZoRC Parameter | normal | obstructive | restrictive |
| $etCO_2U1$ [mmHg] | 45 | 55 | 45 |
| $etCO_2O1$ [mmHg] | 55 | 65 | 55 |
| | Level of ventilation | | |
| mild hyperventilated | Lung mechanic | | |
| ZoRC Parameter | normal | obstructive | restrictive |
| $etCO_2U1$ [mmHg] | n/a | n/a | n/a |
| $etCO_2O1$ [mmHg] | n/a | n/a | n/a |
| | Lung mechanic | | |
| ZoRC Parameter | normal | obstructive | restrictive |
| VTU1 [ml/kg] | 4 | 4 | 2 |
| VTO1 [ml/kg] | 6 | 6 | 4 |

FIG. 13

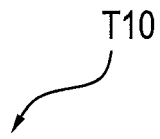

| Classification of Ventilation ($V_T$) (CoV_VT) ||
|---|---|
| $V_T$ | $V_T$-Range |
| very low | $VT < VTU2$ |
| low | $VTU2 < VT < VTU1$ |
| normal | $VTU1 \leq VT \leq VTO1$ |
| high | $VTO2 > VT > VTO1$ |
| very high | $VT > VTO2$ |

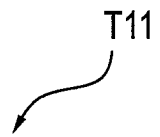

| Classification of Ventilation $etCO_2$ (CoV_etCO2) ||
|---|---|
| $etCO_2$ | $etCO_2$-Range |
| severe hyperventilated | $etCO_2 < etCO_2U2$ |
| mild hyperventilated | $etCO_2U2 < etCO_2 < etCO_2U1$ |
| normoventilated | $etCO_2U1 \leq etCO_2 \leq etCO_2O1$ |
| mild hypoventilated | $etCO_2O2 > etCO_2 > etCO_2O1$ |
| severe hypoventilated | $etCO_2 > etCO_2O2$ |

| Check etCO2 | Check VT | dP | dRR |
|---|---|---|---|
| normo | very low | + 2 mbar | - 2 bpm |
| normo | low | + 1 mbar | - 1 bpm |
| normo | normal | • | • |
| normo | high | - 1 mbar | + 1 bpm |
| normo | very high | - 2 mbar | + 2 bpm |
| mild hyper | very low | • | - 1 bpm |
| mild hyper | low | • | - 1 bpm |
| mild hyper | normal | • | - 1 bpm |
| mild hyper | high | - 1 mbar | • |
| mild hyper | very high | - 2 mbar | • |
| severe hyper | very low | • | - 2 bpm |
| severe hyper | low | • | - 2 bpm |
| severe hyper | normal | • | - 2 bpm |
| severe hyper | high | - 1 mbar | - 1 bpm |
| severe hyper | very high | - 2 mbar | - 1 bpm |
| mild hypo | very low | + 2 mbar | • |
| mild hypo | low | + 1 mbar | • |
| mild hypo | normal | • | + 1 bpm |
| mild hypo | high | • | + 1 bpm |
| mild hypo | very high | • | + 1 bpm |
| severe hypo | very low | + 2 mbar | + 1 bpm |
| severe hypo | low | + 1 mbar | + 1 bpm |
| severe hypo | normal | • | + 2 bpm |
| severe hypo | high | • | + 2 bpm |
| severe hypo | very high | • | + 2 bpm |

VENTILATOR AND PROCESS FOR THE AUTOMATED VENTILATION OF A PATIENT

CROSS REFERENCE TO RELATED APPLICATIONS

This application is a United States National Phase Application of International Application PCT/EP2016/001953, filed Nov. 21, 2016, and claims the benefit of priority under 35 U.S.C. § 119 of German Application 10 2015 015 439.7, filed Dec. 2, 2015, the entire contents of which are incorporated herein by reference.

FIELD OF THE INVENTION

The invention relates to ventilators (also known as respirators) for the automated ventilation (also known as respiration) of a patient. The invention further relates to a process for the automated ventilation of a patient.

BACKGROUND OF THE INVENTION

Ventilators as well as processes with which a pressure control ventilation or a pressure support ventilation of a patient is carried out are known from the state of the art.

Further, it is known that a so-called weaning is carried out within the framework of such a ventilation process, during which the patient is maintained in a so-called comfort zone, and a desired pressure value or a pressure support value is adapted as a function of a detected tidal volume and an end-expiratory carbon dioxide concentration value for the purpose of weaning within the framework of a pressure support ventilation. Such processes are also known as so-called "Smart-Care/PS" processes.

SUMMARY OF THE INVENTION

The object of the present invention is to carry out a pressure control ventilation or pressure support ventilation of a patient, wherein it is made possible in an improved and automated manner to reach a state of ventilation that is possibly advantageous for the patient.

A ventilator according to the present invention for the automated ventilation of a patient, comprises an expiratory port and an inspiratory port for connecting a ventilation tube facing the patient for a breathing gas, a breathing gas delivery unit, at least one volume flow sensor for detecting a volume flow of the breathing gas, at least one breathing gas sensor for detecting a carbon dioxide concentration in the breathing gas, at least one pressure sensor for detecting a pressure of the breathing gas, as well as at least one computer, wherein the computer is configured to actuate the breathing gas delivery unit as a function of the detected pressure and of a preset desired pressure value, wherein the computer is further configured to perform an adaptation of the desired pressure value and an adaptation of a ventilation rate as a function of the detected volume flow and as a function of the detected carbon dioxide concentration.

The ventilator according to the present invention is advantageous because the computer is not only configured to perform an adaptation of the desired pressure value as a function of a detected volume flow and as a function of a detected carbon dioxide concentration, but it is also configured to perform an adaptation of the ventilation rate as a function of the detected volume flow and as a function of the detected carbon dioxide concentration. An improved form of ventilation of the patient is possibly achieved hereby within the framework of the automated ventilation, which is preferably a pressure control ventilation or a pressure support ventilation. The ventilation is consequently changed not only in terms of the desired pressure value, but also in terms of a ventilation rate that is to be taken into consideration.

The computer is preferably configured to actuate the breathing gas delivery unit as a function of the detected pressure, of the preset desired pressure value and further of the ventilation rate, the computer being further configured to actuate the breathing gas delivery unit such that the automated ventilation is carried out as a pressure control ventilation. This embodiment of the present invention is advantageous because the ventilation rate is used within the framework of the pressure control ventilation to actuate the breathing gas delivery unit by the computer.

The computer is preferably configured to actuate the breathing gas delivery unit such that the automated ventilation is carried out as a pressure support ventilation, wherein the computer is configured to control the output of a warning signal as a function of the ventilation rate. This embodiment of the present invention is advantageous because the output of the warning signal as a function of the ventilation rate depends on the manner in which the computer had adapted before the ventilation rate as a function of the detected volume flow and as a function of the detected carbon dioxide concentration. Such a warning signal may then possibly be used by the clinician as an indication, whereby the clinician will possibly consider a change in the automated ventilation.

The computer is preferably configured to determine a tidal volume fed to the patient on the basis of the detected volume flow, further to determine an end-expiratory carbon dioxide concentration etCO2 and to perform the adaptation of the ventilation rate as a function of the determined tidal volume and of the determined end-expiratory carbon dioxide concentration. The computer is preferably configured now to perform the adaptation of the desired pressure value and the adaptation of the ventilation rate as a function of the determined tidal volume, a target tidal volume, the determined end-expiratory carbon dioxide concentration and a target carbon dioxide concentration. Regulation of the tidal volume and of the end-expiratory carbon dioxide concentration to the respective target values is achieved hereby.

The computer is preferably configured to perform the adaptation of the desired pressure value and the adaptation of the ventilation rate as a function of the determined tidal volume, of an upper volume limit value, of a lower volume limit value, of the determined end-expiratory carbon dioxide concentration, of an upper concentration limit value and of a lower concentration limit value. These embodiments of the present invention are advantageous because a so-called comfort zone is defined for the ventilation of the patient by the respective limit values relative to the tidal volume and the end-expiratory carbon dioxide concentration, and the adaptation of the ventilation rate and of the desired pressure value is carried out by a comparison of this comfort zone and the tidal volume, on the one hand, as well as of the end-expiratory carbon dioxide concentration in order to maintain the patient within this comfort zone during the ventilation. This comfort zone may possibly be advantageous for the patient and possibly represent an adequate ventilation. This is achieved by the adaptation of the ventilation rate and of the desired pressure value being adapted as a function of two parameters, namely, the tidal volume and the end-expiratory carbon dioxide concentration, as well as of the defined comfort zone, defined by the limit values.

The computer is preferably configured to actuate the breathing gas delivery unit as a function of the detected pressure, of the preset desired pressure value and further of the ventilation rate, and further to actuate the breathing gas delivery unit such that the automated ventilation is carried out as a pressure control ventilation, further to detect a spontaneous breathing activity of the patient on the basis of the detected volume flow, and finally to adapt the concentration limit values as a function of the detection result. This embodiment of the present invention is advantageous because possible and possibly undesired attempts made by the patient at spontaneous breathing can possibly be counteracted by an adaptation of the concentration limit values in the course of a pressure control ventilation.

The computer is preferably configured to select the upper volume limit value, the lower volume limit value, the upper concentration limit value and the lower concentration limit value as a function of a specification concerning a property of the lungs of the patient. This embodiment is advantageous because the comfort zone defined by means of the limit values can take a property of the lungs of a patient into consideration. This lung property may be preset or entered by a specification made by a clinician.

The computer is preferably configured to select, further, the upper concentration limit value and the lower concentration limit value as a function of a specification concerning a desired gas exchange rate of the patient. This embodiment is advantageous because a definition of the comfort zone can be selected by means of the concentration limit values as a function of a specification made by a clinician concerning a desired gas exchange rate of a patient. Such a gas exchange rate is characterized, for example, by a so-called normal ventilation of a patient or else, for example, by a mild hyperventilation of a patient. Therefore, a gas exchange rate is, in other words, a degree of ventilation of a patient.

The upper volume limit value is preferably a first upper volume limit value, and the lower volume limit value is further a first lower volume limit value, and the computer is further configured to perform the adaptation of the desired pressure value and the adaptation of the ventilation rate as a function of a second upper volume limit value and of a second lower volume limit value. This embodiment of the present invention is advantageous because not only is the adaptation of the desired pressure value as well as the adaptation of the ventilation rate performed rigidly on the basis of respective first upper and first lower limit values relative to the tidal volume, but a degree of a deviation of the tidal volume from the first limit values can be taken into consideration based on the fact that the second volume limit values are taken into consideration for the adaptation.

The upper concentration limit value is preferably a first upper concentration limit value, and the lower concentration limit value is further a first lower concentration limit value, and the computer is further configured to perform the adaptation of the desired pressure value and the adaptation of the ventilation rate as a function of a second upper concentration limit value and of a second lower concentration limit value. This embodiment of the present invention is advantageous because not only is the adaptation of the desired pressure value as well as the adaptation of the ventilation rate performed rigidly on the basis of respective first upper and first lower limit values relative to the end-expiratory carbon dioxide concentration, but a degree of a deviation of the end-expiratory carbon dioxide concentration from the first limit values can also be taken into consideration for the adaptation on the basis of the second concentration limit values.

Further, a process is proposed for the automated ventilation of a patient, comprising the steps: Feeding a breathing gas to a patient via an inspiratory port and returning the breathing gas via an expiratory port by operating a breathing gas delivery unit; detection of a volume flow of the breathing gas by means of at least one volume flow sensor; detection of a carbon dioxide concentration in the breathing gas by means of at least one breathing gas sensor; detection of a pressure of the breathing gas by means of at least one pressure sensor; actuation of the breathing gas delivery unit as a function of the detected pressure and of a preset desired pressure value by means of at least one computer; as well as adaptation of the desired pressure value and adaptation of a ventilation rate as a function of the detected volume flow and as a function of the detected carbon dioxide concentration by means of the computer.

A computer may further be provided for a ventilator for the automated ventilation of a patient, which computer is configured to detect a volume flow signal, which indicates a volume flow of a breathing gas; for detecting a carbon dioxide concentration signal, which indicates a carbon dioxide concentration in the breathing gas; for detecting a pressure signal, which indicates a pressure of the breathing gas, as well as for providing an actuating signal for a breathing gas delivery unit. The computer is configured to determine the actuating signal as a function of the detected pressure signal and of a preset desired pressure value, as well as to perform an adaptation of the desired pressure value and an adaptation of a ventilation rate as a function of the detected volume flow signal; and as a function of the detected carbon dioxide concentration signal.

Proposed is further a process for operating a ventilator for the automated ventilation of a patient, comprising the steps: Detection of a volume flow signal, which indicates a volume flow of a breathing gas; detection of a carbon dioxide concentration signal, which indicates a carbon dioxide concentration in the breathing gas; detection of a pressure signal, which indicates a pressure of the breathing gas; provision of an actuating signal for the breathing gas delivery unit as a function of the detected pressure signal and of a preset desired pressure value; as well as adaptation of the desired pressure value and adaptation of a ventilation rate as a function of the detected volume flow signal and as a function of the detected carbon dioxide concentration signal. This process is preferably carried out with a computer program on at least one computer. Proposed is further a program with a program code for carrying out the above-mentioned process when the program code is executed on a computer, on a processor or on a programmable hardware component.

Advantages of the ventilator being proposed likewise apply to the process being proposed for the automated ventilation of a patient. These advantages likewise apply to the computer proposed for a ventilator for the automated ventilation of a patient. These advantages also apply to a process for operating a ventilator for automated ventilation as well as to the proposed program with a program code.

The present invention will be explained in more detail below on the basis of special embodiments based on the figures without limitation of the general inventive features.

The present invention is described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 12a is a table with limit values for carrying out the process according to the present invention according to the first embodiment;

FIG. 12b is a table with limit values for carrying out the process according to the present invention according to the second embodiment;

FIG. 13 is a table with limit values for carrying out the process according to the present invention according to the third embodiment;

FIG. 14 is a view with tables for determining degrees of ventilation or gas exchange rates relative to a tidal volume or an end-expiratory carbon dioxide concentration;

FIG. 15 is a table with values for adapting the desired pressure value and for adapting the ventilation rate;

DESCRIPTION OF THE PREFERRED EMBODIMENTS

Figure 1:
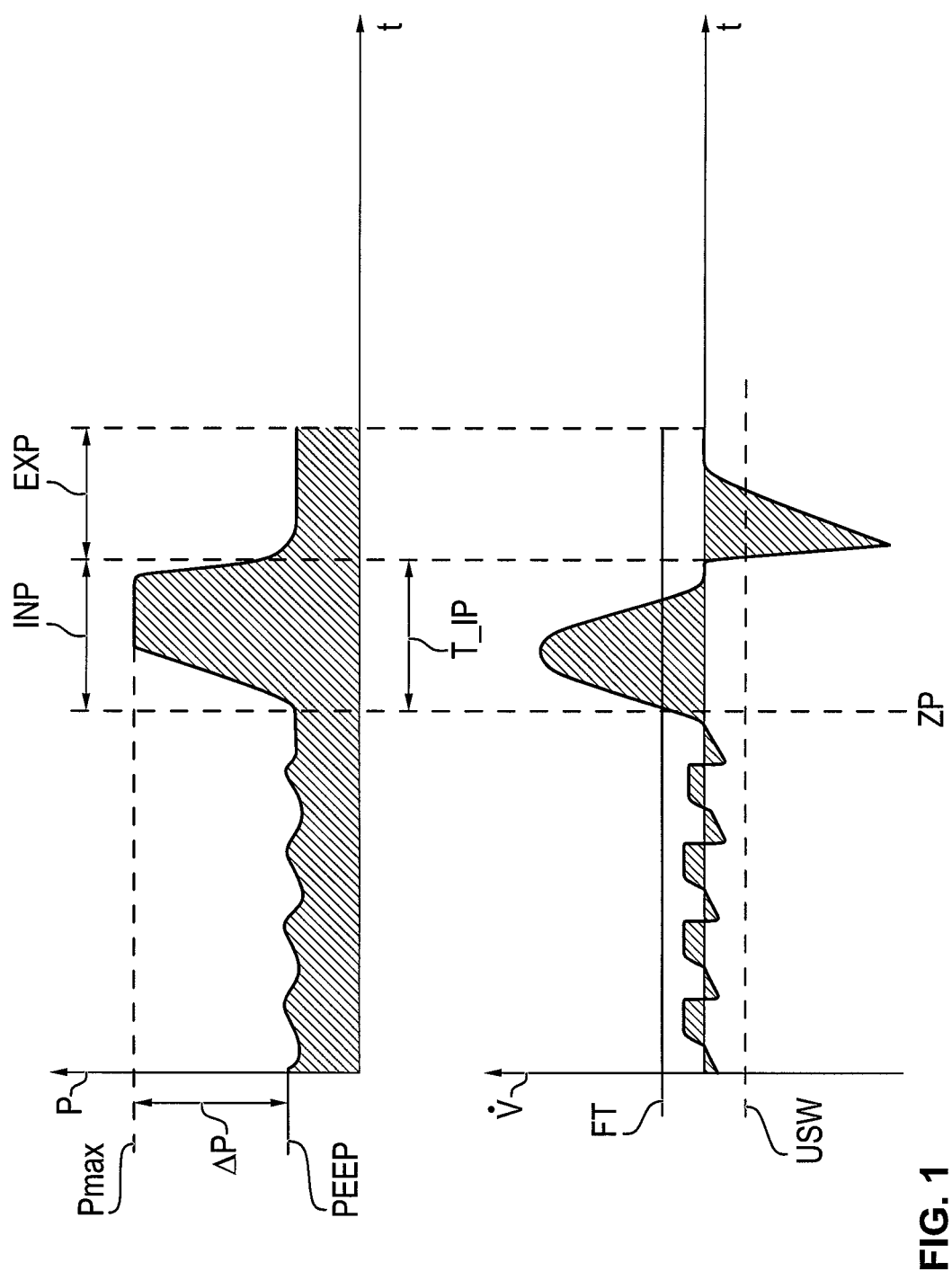
FIG. 1 is a graph view showing a pressure curve over time as well as a volume flow curve over time in the course of an inhalation and an inhalation.

Referring to the drawings, FIGS. 1 through 4 show curves known from the state of the art, on the basis of which the principles of a trigger control, of a pressure support ventilation, of a pressure control ventilation without permitting attempts at spontaneous breathing as well as of a pressure control ventilation with attempts at spontaneous breathing being permitted will be explained. These principles can also be found in the document "*Modes of ventilation in Intensive Care,*" Karin Deden, Dräger Medical GmbH. Principles of pressure control ventilation as well as of pressure support ventilation can also be found in the document "*Zeus Infinity Empowered*" manual, Dräger Medical AG & Co. KG, 1st edition, February 2009.

FIG. 1 shows for the illustration of a trigger control a pressure curve of a pressure value P over time, and it also shows a curve of a volume flow $\dot{V}$ over time. If a patient is ventilated by a ventilator, the pressure is controlled such that the pressure is regulated to an at least end-expiratory pressure PEEP (Positive End Expiratory Pressure) prior to an inspiratory phase INP. If a patient is making an attempt at spontaneous breathing, this leads to the volume flow $\dot{V}$ being exceeded over a so-called trigger threshold or flow trigger threshold FT at the time ZP. When the threshold is exceeded, the pressure P is then regulated such that the pressure P is regulated to a maximum pressure Pmax, and this maximum pressure Pmax is higher than the minimum pressure PEEP by a pressure difference $\Delta P$. A duration T_IP is usually preset for an inspiratory phase, so that the expiratory phase EXP is then started after the end of the duration T_IP, during which the pressure P is again reduced to the minimum pressure PEEP. Thus, a negative volume flow $\dot{V}$ is obtained during the expiratory phase based on the flow of the volume flow $\dot{V}$ out of the patient.

Figure 3:
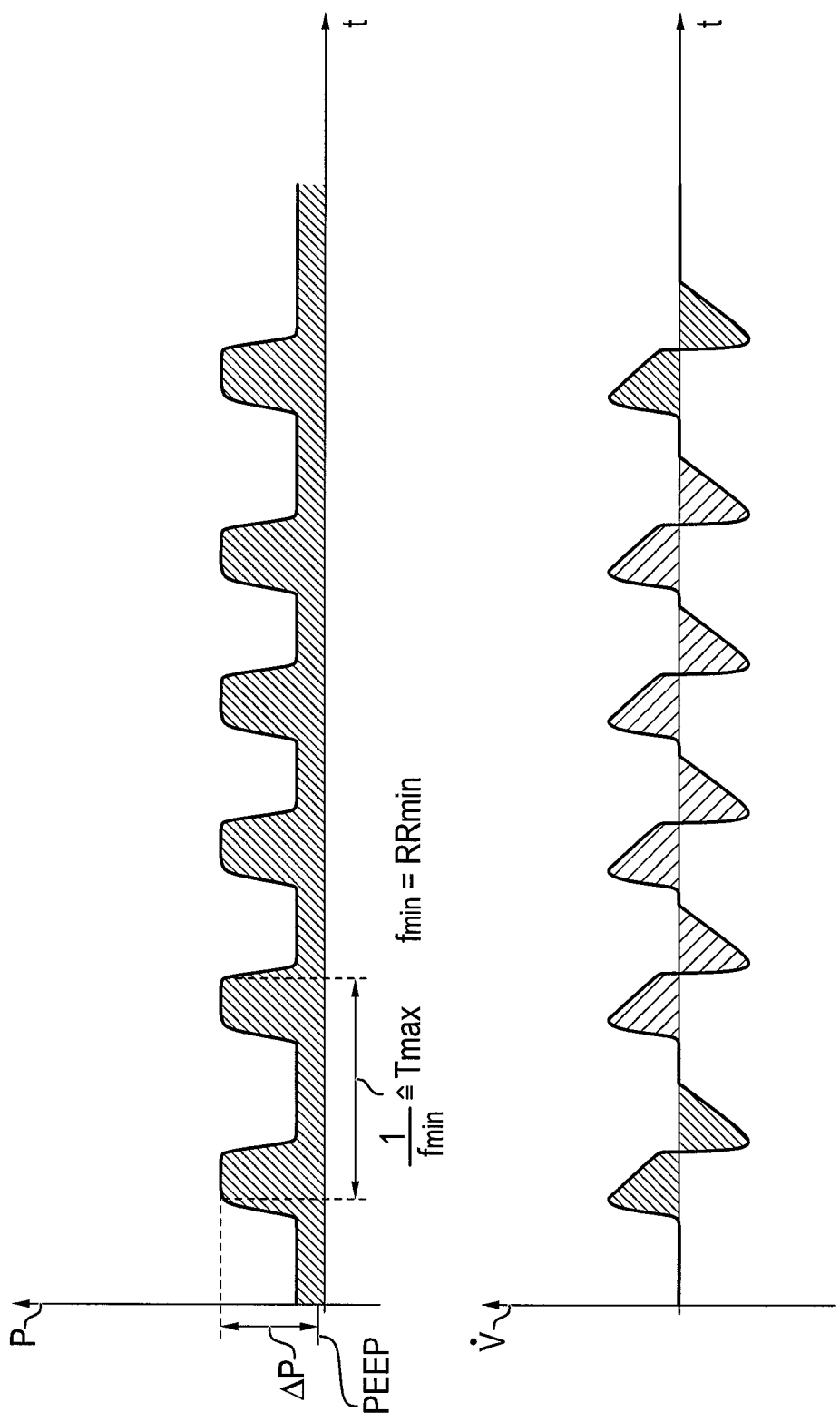
FIG. 3 is a graph view showing a pressure curve over time as well as a volume flow curve over time within the framework of a pressure support ventilation, which takes place within the framework of attempts at spontaneous breathing by a patient.

Such a trigger-controlled ventilation is usually carried out within the framework of a pressure support ventilation, as it is also shown once again in FIG. 3. Such a pressure support ventilation if carried out, furthermore, preferably such that the patient must bring about a minimum breathing frequency fmin or RRmin based on the triggering initiated by him, so that a maximum time window Tmax is obtained between two start times of contiguous inspiratory phases. If the ventilation triggered by the patient leads to the absence of a repeated inhalation after the end of the time window Tmax or his own breathing frequency is lower than the minimum breathing frequency RRmin, a warning may be outputted in such a case. Such a warning may be considered by a clinician to be an indication that a change in the automated ventilation should possibly be considered.

Figure 2:
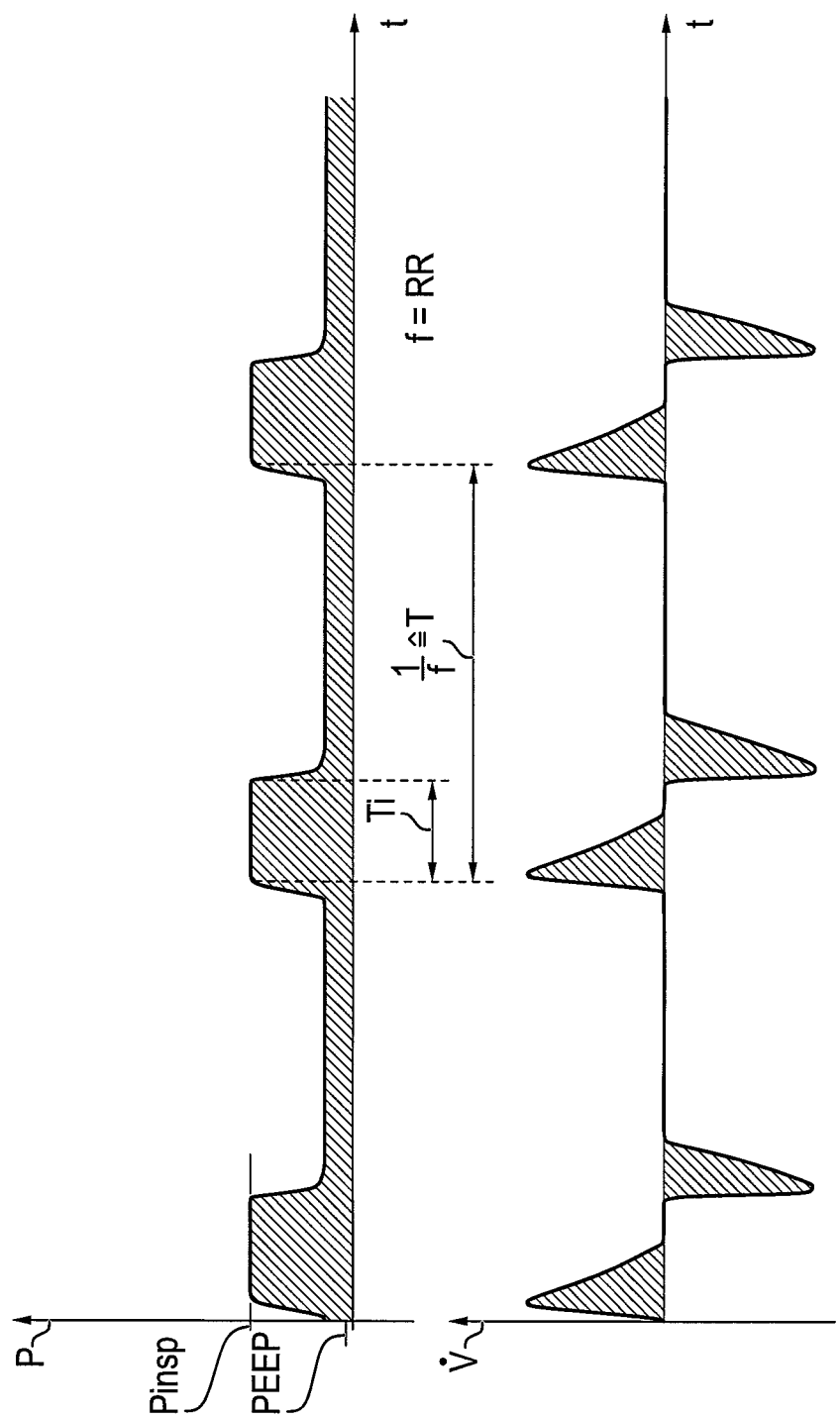
FIG. 2 is a graph view showing a pressure curve over time as well as a volume flow curve over time within the framework of a pressure control ventilation, during which no attempts at spontaneous breathing by a patient are permitted.

FIG. 2 shows a pressure curve P over time as well as a volume flow curve $\dot{V}$ over time for the case of a pressure control ventilation, during which no attempts at spontaneous breathing by a patient are permitted. A fixed duration Ti is now set for an inspiratory phase as well as a ventilation rate for RR. The rate f or RR defines here the time difference T between two starts of respective contiguous inspiratory phases. If an inspiratory phase begins, the pressure is controlled or regulated starting from the minimum PEEP to a maximum pressure value or desired pressure value Pinsp.

Figure 4:
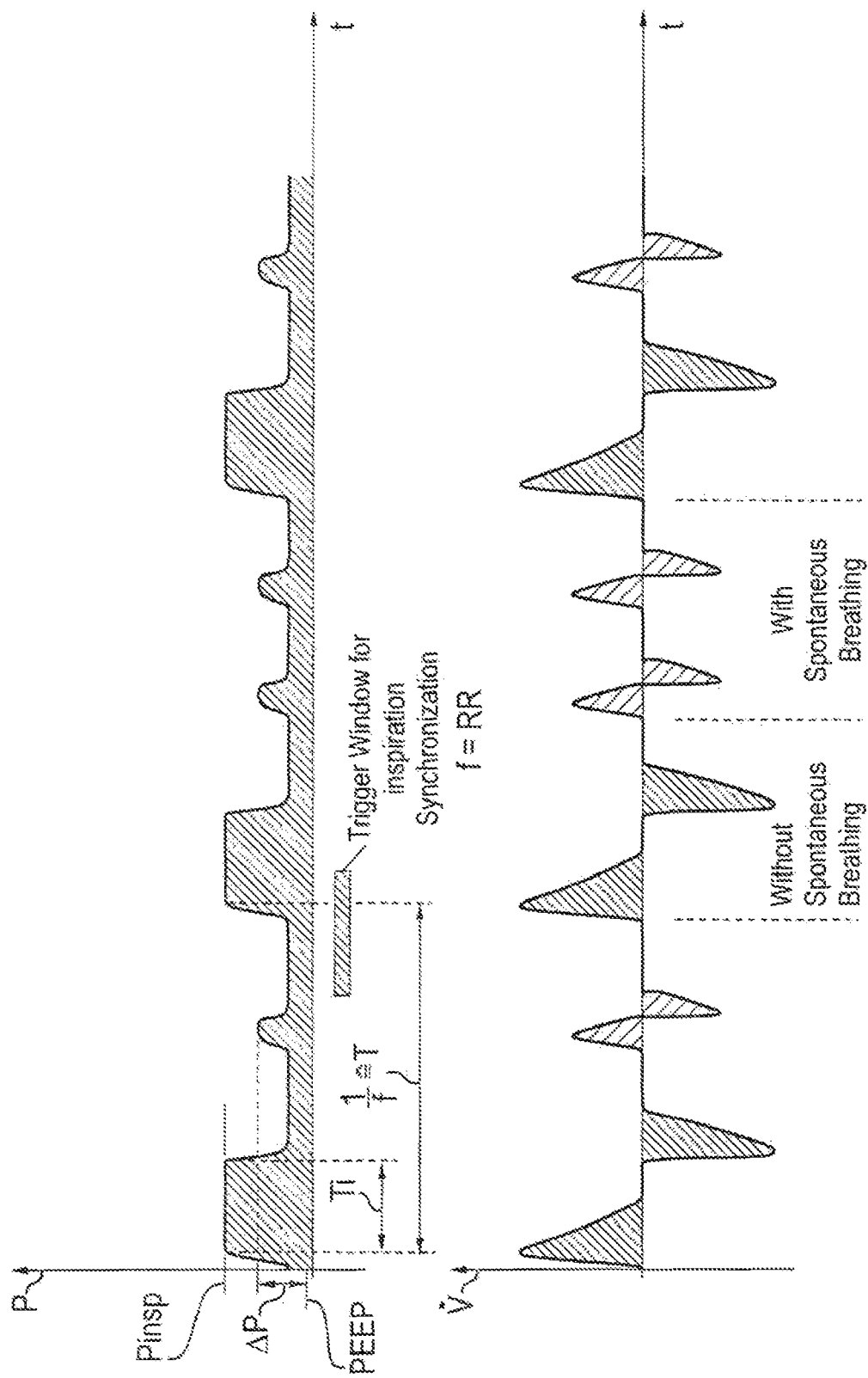
FIG. 4 is a graph view showing a pressure curve over time as well as a volume flow curve over time within the framework of a pressure control ventilation, during which attempts at spontaneous breathing by a patient are permitted.

FIG. 4 shows the principle of a pressure control ventilation, during which attempts at spontaneous breathing by a patient are also permitted with flow triggering by the patient for a pressure support. Consequently, there are inspiratory phases with the previously explained pressure control, during which the pressure P is controlled to the desired pressure value Pinsp. Further, there are inspiratory phases with pressure support based on triggering caused by the patient on the basis of spontaneous breathing, during which a support or control of the pressure value to a pressure level that is higher than the minimum pressure PEEP by the pressure difference ΔP takes place.

Figure 5:
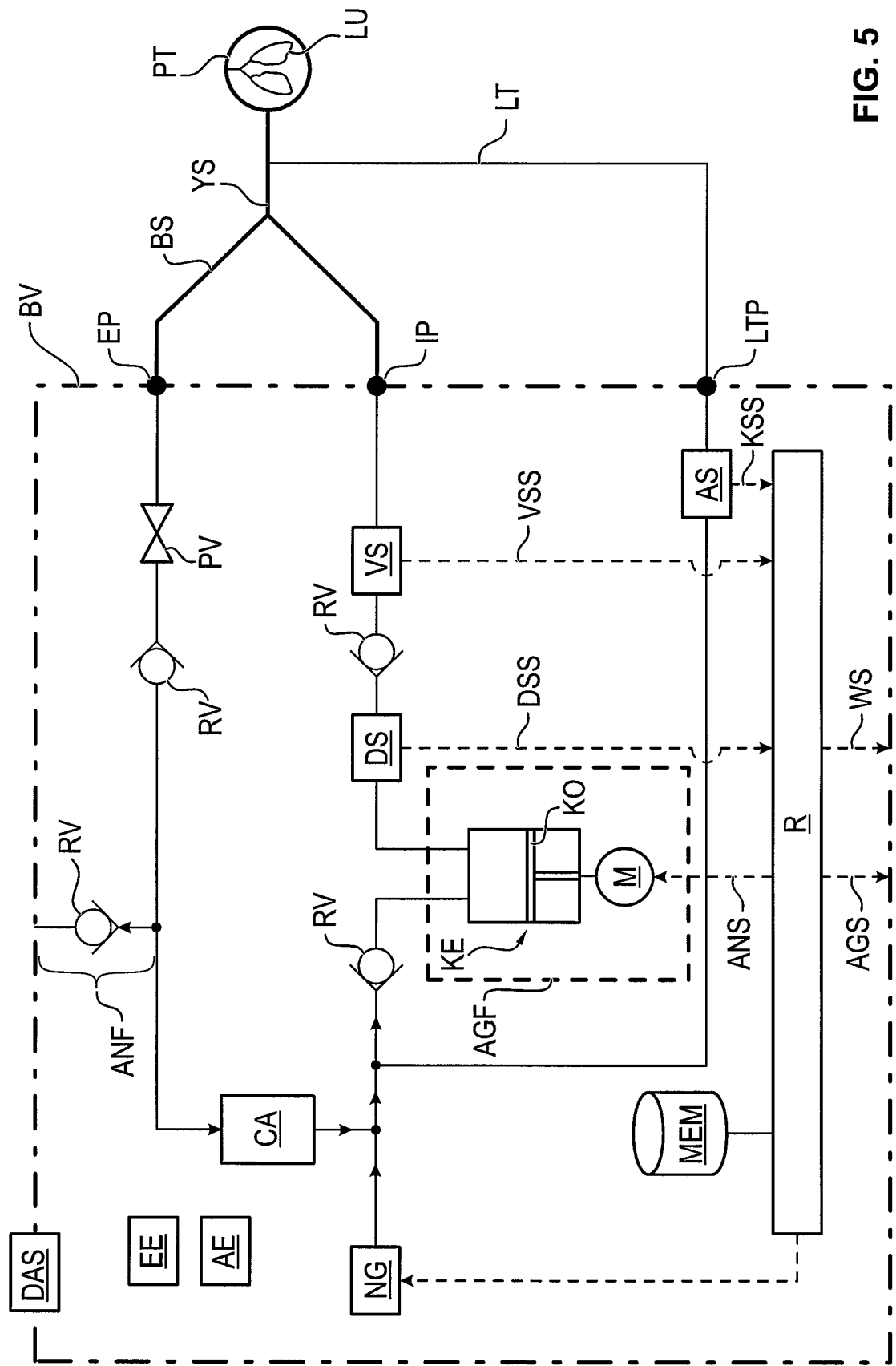
FIG. 5 is a schematic view shows a ventilator according to the present invention.

FIG. 5 shows the device BV for the automated ventilation of a patient PT according to the present invention. The ventilator BV according to the present invention has an inspiratory port IP and an expiratory port EP, to which a breathing tube BS, which faces the patient PT, can be connected. A breathing gas is fed to the patient and also removed from the patient to the device BV via this breathing tube BS. The feeding takes place via the inspiratory port IP and the removal takes place via the expiratory port EP. The ventilation tube BS merges the connections of the ports EP, IP at a so-called Y-piece YS, which then usually ends at a tube, which is inserted into the patient PT in order to ventilate him via his lungs LU.

The ventilator BV further has a breathing gas delivery unit AGF. The breathing gas delivery unit AGF is preferably a reciprocating pump KE, in which a piston KO can be moved to and fro by a motor M.

The ventilator BV has at least one volume flow sensor VS for detecting a volume flow of the breathing gas. The volume flow sensor VS can provide a volume flow sensor signal VSS for a computer R. The computer R is at least one computer, which may also be embodied by a network of a plurality of computers.

The ventilator BV further has a pressure sensor DS for detecting a pressure of the breathing gas. The pressure sensor DS provides a pressure sensor signal DSS for the computer R.

A minimum pressure PEEP is preferably generated by a valve PV, which is preferably located in the area of the expiratory port EP.

The ventilator BV further has a breathing gas sensor AS for detecting a carbon dioxide concentration in the breathing gas. The sensor AS is preferably provided behind a measuring line LT, which removes a measuring sample of the breathing gas at the Y-piece YS and is connected to a measured gas port LTP. The breathing gas sensor provides a carbon dioxide concentration signal KSS for the computer R. The computer R is configured to actuate the breathing gas delivery unit AGF by means of an actuating signal ANS.

In the preferred case in which the ventilator BV is an anesthesia ventilator, the ventilator BV preferably has a carbon dioxide absorber CA as well as an anesthetic gas mixing unit NG. A gas mixture necessary for the anesthesia can now be introduced into the closed breathing circuit via the anesthetic gas-mixing unit NG. Furthermore, the ventilator BV preferably has as an anesthesia ventilator an anesthetic gas discharge line AN or a port to an anesthetic gas discharge line AN. The gas flow within the ventilator BV is preferably controlled by nonreturn valves RV. The computer R preferably controls the anesthetic gas mixing unit NG by means of a control signal NGAS.

The ventilator BV from FIG. 5 preferably has an input unit EE or an interface for an input unit EE, by means of which inputs, which can be made by an operator or clinician, can be received at the ventilator BV.

The computer R preferably accesses a memory unit MEM in order to carry out the processes according to the present invention.

The computer R may, furthermore, preferably output a warning signal WS. This preferably happens via a data interface DAS of the device BV.

The ventilator according to the present invention is configured to carry out a pressure control ventilation or a pressure support ventilation of the patient PT.

Figure 6:
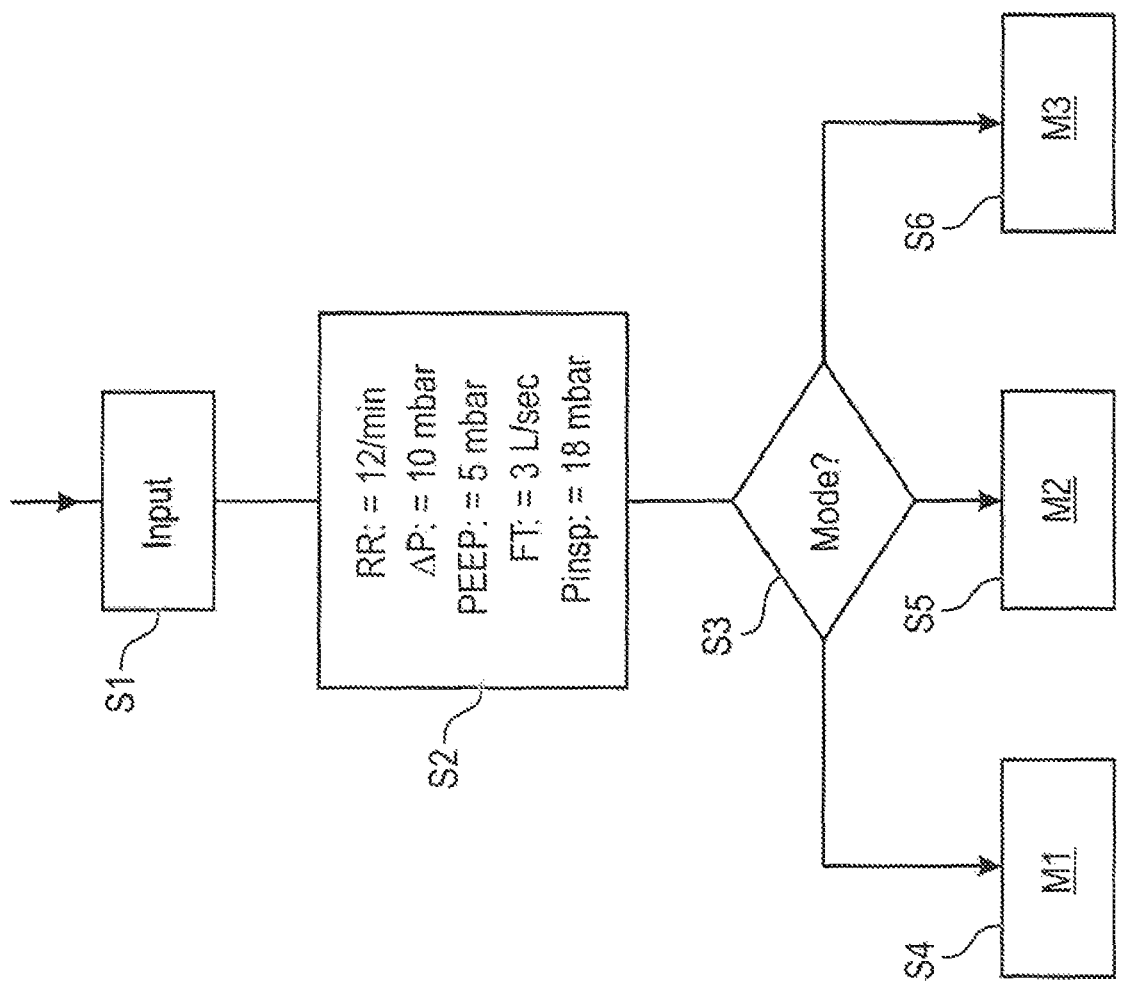
FIG. 6 is a flow diagram showing process steps for initializing and initiating different embodiments of the process according to the present invention.

FIG. 6 shows initiation steps, by means of which the ventilator from FIG. 5 can be prompted to carry out different embodiments of the process according to the present invention. Specifications are inputted by a user or clinician in a step S1.

Figure 11:
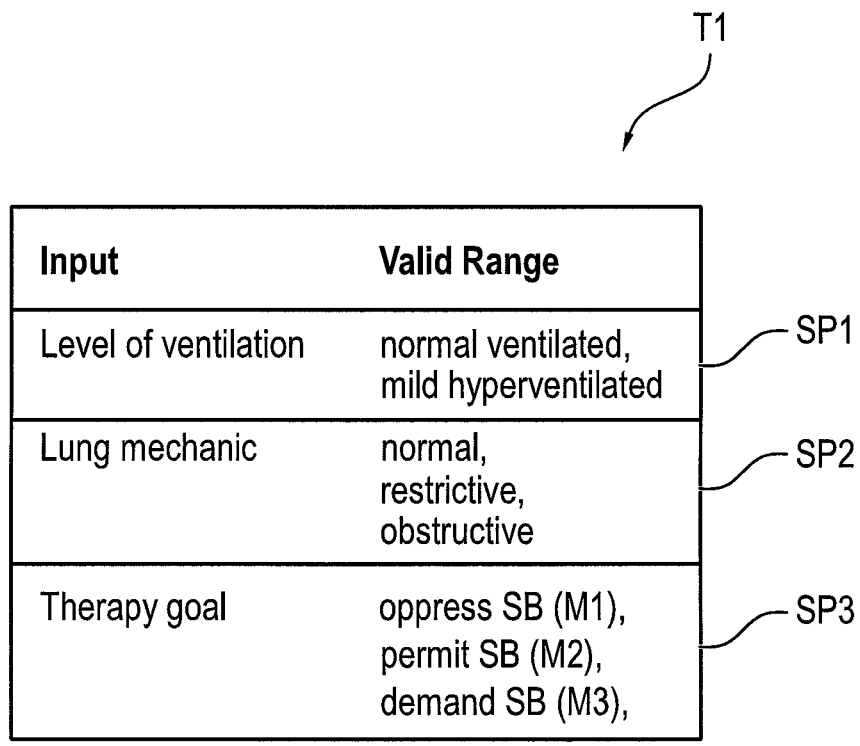
FIG. 11 is a table with preset values that can be specified by a clinician.

In Table T1, FIG. 11 shows possibilities of different inputs within the framework of step S1 of FIG. 6. The first column SP1 contains different entries or specifications, by means of which a desired degree of ventilation or a desired gas exchange rate of a patient can be selected. These are preferably the variants of a normal ventilation or of a mild hyperventilation.

The second column SP2 of FIG. 11 contains, furthermore, various possibilities of specifications concerning lung properties ("Lung Mechanic") of the patient. The specifications may indicate the properties of normal lungs, of restrictive lungs or of obstructive lungs.

Further, the third column SP3 of FIG. 11 shows possibilities of specifications, by means of which a selection of one of the three embodiments of the process according to the present invention can be preset. A selection of suppressing a spontaneous breathing ("oppress spontaneous breathing (SB)") indicates a selection of the first embodiment M1 of the process according to the present invention, in which attempts at spontaneous breathing by the patient in the course of a purely pressure control ventilation are suppressed. A selection of permitting spontaneous breathing ("permit spontaneous breathing (SB)") indicates a selection of the second embodiment M2 of the process according to the present invention, in which attempts at spontaneous breathing by the patient are permitted. A selection of the demand for spontaneous breathing ("demand spontaneous breathing (SB)") indicates a selection of the third embodiment M3 of the process according to the present invention, in which attempts at spontaneous breathing by the patient are compulsorily demanded or presumed in the course of a purely pressure support ventilation.

An alternative designation "Controlled Ventilation" may also be used instead of the designation "oppress spontaneous breathing (SB)." An alternative designation "Augmented Ventilation" may also be used instead of the designation "permit spontaneous breathing (SB)." An alternative designation "Forced Spontaneous Breathing" may also be used instead of the designation "demand spontaneous breathing (SB)."

The computer is preferably configured to provide an output signal AGS to a display unit AE, so that the display unit AE displays information in an optical representation, which represents one or more of the aforementioned specifications to a viewer for a selection. The output signal AGS is preferably outputted via a data interface DAS for the purpose of displaying the specifications on a display unit, which is not an integral part of the device BV.

A selection of one or more of the above-mentioned specifications by a user or clinician may also be received by the interface EE or input unit EE of the ventilator BV, which is shown in FIG. 5. This input unit EE may preferably be an input interface EE belonging to or communicating with the ventilator BV, the input unit being, e.g., a keyboard, a touchscreen, a rotary pushbutton and/or a computer mouse.

Coming back to FIG. 6, initialization of ventilation-relevant parameters can be performed in step S2. The ventilation rate is preferably set here at 12 breaths per minute, the possibly necessary pressure difference ΔP is set at 10 mbar, the minimum pressure PEEP at 5 mbar, the trigger threshold FT at 3 L/sec, and the possibly necessary maximum pressure value Pinsp at 18 mbar. It is clear to a person skilled in the art that the values being shown here are only exemplary values and they may also be selected differently when the process according to the present invention is carried out and the device according to the present invention is embodied.

The process according to the present invention may now be branched off in a step S3 depending on an input or a selection of a specification from step S1 with respect to a selected embodiment M1, M2, M3 of the process according to the present invention into one of the respective steps S4, S5, S6.

Figure 7:
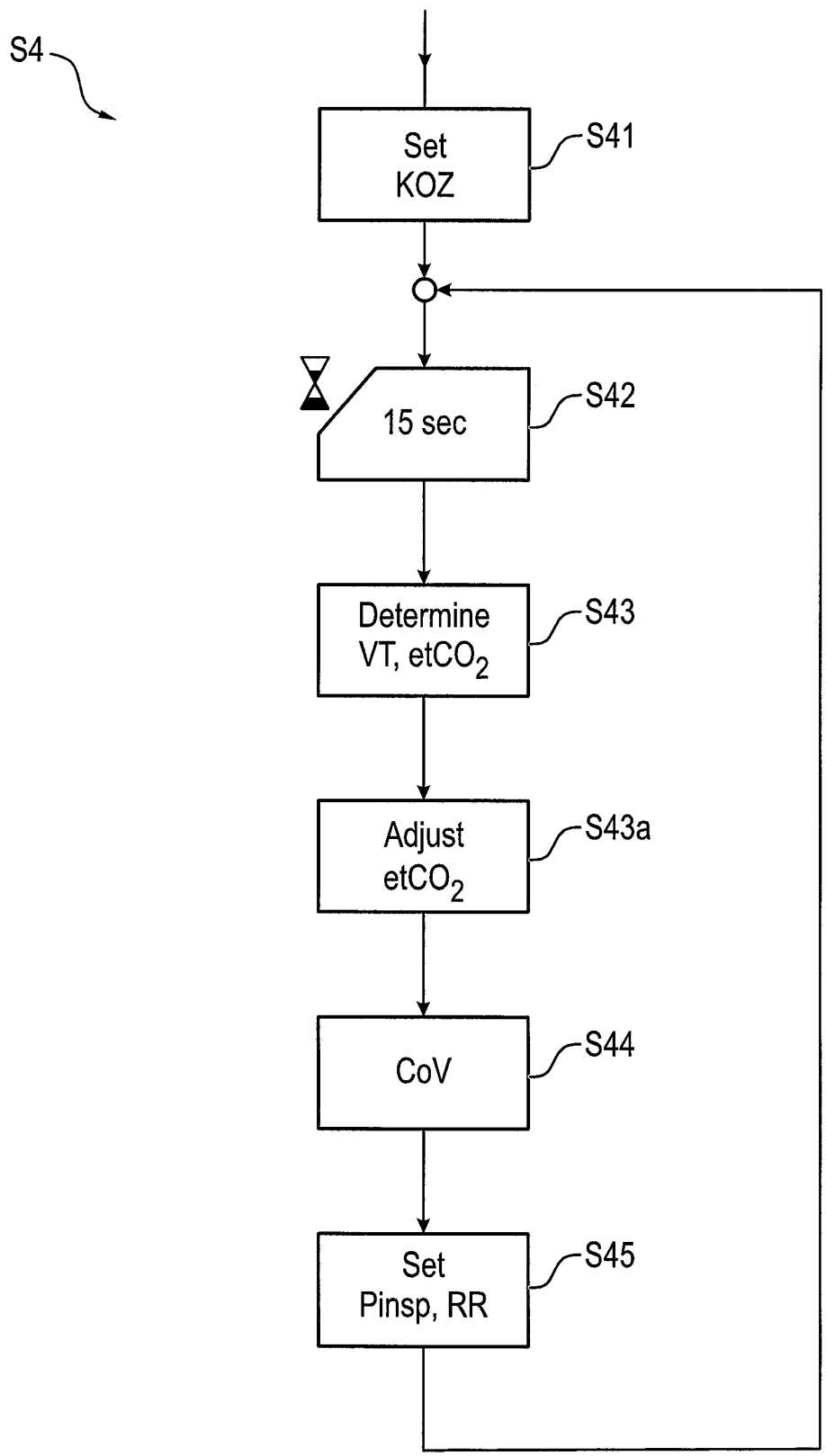
FIG. 7 is a flow diagram showing process steps according to a first embodiment of the process according to the present invention.

FIG. 7 shows the process step S4, in which the first embodiment M1 of the process according to the present invention is carried out, in which case the ventilation is a pressure control ventilation without attempts at spontaneous breathing by the patient being permitted.

Figure 8:
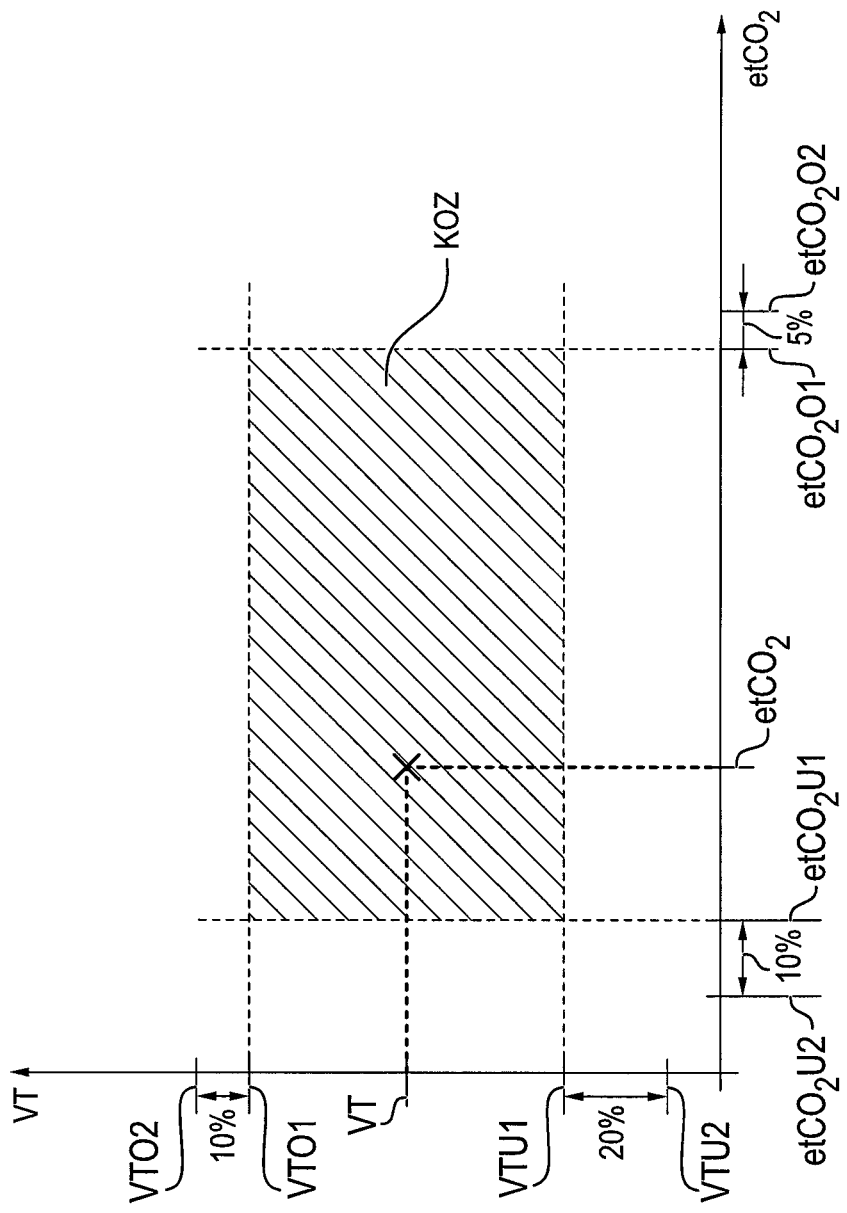
FIG. 8 is a graph view with an illustration of limit values.

Limit values or so-called comfort zone KOZ are defined in a first partial process step S41. FIG. 8 can be viewed in this connection corresponding to this step S41.

FIG. 8 indicates the comfort zone KOZ, which is given whenever a tidal volume VT inhaled by the patient, which is between an upper volume limit value VTO1 and a lower volume limit value VTU1, is determined by the computer from the detected volume flow. Further, to reach the comfort zone KOZ, it is necessary for the end-expiratory carbon dioxide concentration etCO2, which is between an upper concentration limit value etCO2O1 and a lower concentration limit value etCO2U1 and is determined by the computer R on the basis of the carbon dioxide concentration signal KSS, to be present.

A goal that can possibly be reached is to ventilate the patient such that due to the ventilation, the patient has or breathes a tidal volume VT which is within the volume limit values VTO1, VTU1, and that an end-expiratory carbon dioxide concentration etCO2 is also between the concentration limit values etCO2U1 and etCO2O1 at the same time.

In reference to the partial step S41 of FIG. 7, the manner in which the respective volume limit values VTO1, VTU1 as well as the respective concentration limit values etCO2U1, etCO2O1 can be selected can be determined using FIG. 12a and viewing Table T2.

The computer R according to FIG. 5 determines a tidal volume inhaled by the patient on the basis of the determined volume flow. On the basis of the detected volume flow and a preset duration Ti of the inspiratory phase, the computer preferably determines for this the tidal volume as an integral value of the volume flow over this duration Ti. As an alternative, a duration of an inspiratory phase can be determined such that a start of the inspiratory phase is inferred from the fact that a volume flow threshold value FT is exceeded, and an end of the inspiratory phase is inferred when the actual value subsequently drops below the volume flow threshold value FT.

Based on the detected carbon dioxide concentration, the computer determines an end-expiratory carbon dioxide concentration. An end of an end-expiratory phase is then inferred preferably by a comparison of the volume flow, as is shown in FIG. 1, and of a lower or negative USW threshold value if the detected volume flow passes through the lower threshold value from below.

The values determined by the computer R according to FIG. 5 for the tidal volume as well as for the end-expiratory carbon dioxide concentration are preferably provided as measured values every 4 sec. According to the partial step S42 of FIG. 7, there is at first a waiting period of 15 sec, after which the tidal volume VT being considered is determined within the framework of partial step S43 by means of a median filtering of the measured values of the tidal volume that were available in the last 60 sec. The end-expiratory carbon dioxide concentration etCO2 taken into consideration is likewise determined by means of a preprocessing, preferably median filtering, on the basis of the measured values of the end-expiratory carbon dioxide concentration that represent the last 60 sec.

The carbon dioxide limit values are preferably adapted in partial step S43a. This will be explained later in reference to FIG. 16.

It will now be explained at first in what manner an adaptation of the ventilation rate RR as well as an adaptation of the desired pressure value Pinsp are performed as a function of the detected volume flow or of the tidal volume VT and as a function of the detected carbon dioxide concentration and of the end-expiratory carbon dioxide concentration etCO2. Since the ventilation is a pressure control ventilation according to the embodiment of the process in reference to FIG. 7, the pressure value Pinsp is adapted here as a desired pressure value and the value RR is adapted as the ventilation rate.

After determining the tidal volume VT as well the end-expiratory carbon dioxide concentration etCO2 within the framework of partial step S43, a degree of ventilation is determined within the framework of partial step S44 in reference to the tidal volume and, further, a degree of ventilation is determined in reference to the end-expiratory carbon dioxide concentration.

FIG. 14, which specifies various degrees of ventilation in Table T10 by comparing the tidal volume VT with the previously determined limit values, is to be used for this. Not only the upper limit value and the lower limit value, VTO1, VTU1, respectively, are used here, as was previously shown in Table T2, but additional, second limit values VTO2, VTU2 are used as well. These second limit values VTO2, VTU2 are likewise shown in FIG. 8. Consequently, respective second limit values VTO2, VTU2 are used, in which a deviation by 10% or 20% from the first limit values VTO1, VTU1 is taken into consideration.

Corresponding statements can also be made for the degree of ventilation or the gas exchange rate in reference to the end-expiratory carbon dioxide concentration compared to the concentration values etCO2U1, etCO2O1 as well as further second concentration values etCO2U2, etCO2O2, which deviate from the first concentration values etCO2U1, etCO2O1 by 5% and 10%, respectively, and are likewise shown in FIG. 8.

Coming back to FIG. 7, it can now be stated that the desired pressure value Pinsp as well as the ventilation rate RR are adapted in partial step S45. This is carried out with the use of a Table T20 from FIG. 15. Using the degrees of ventilation determined on the basis of Table 10 and Table 11 of FIG. 14 in reference to the tidal volume VT and to the end-expiratory carbon dioxide concentration etCO2, a change dP in the pressure value Pinsp as well as a change dRR in the ventilation rate RR can now be determined on the basis of Table 20 of FIG. 15. The desired pressure value Pinsp as well as the ventilation rate are then adapted on the basis of the determined changes dP as well as dRR. This is carried out according to $$Pinsp:=Pinsp+dP$$

$$RR:=RR+dRR.$$

The process according to FIG. 7 from the embodiment of a pressure support ventilation without spontaneous breathing activity of the patient then returns to the partial process step S42.

Figure 16:
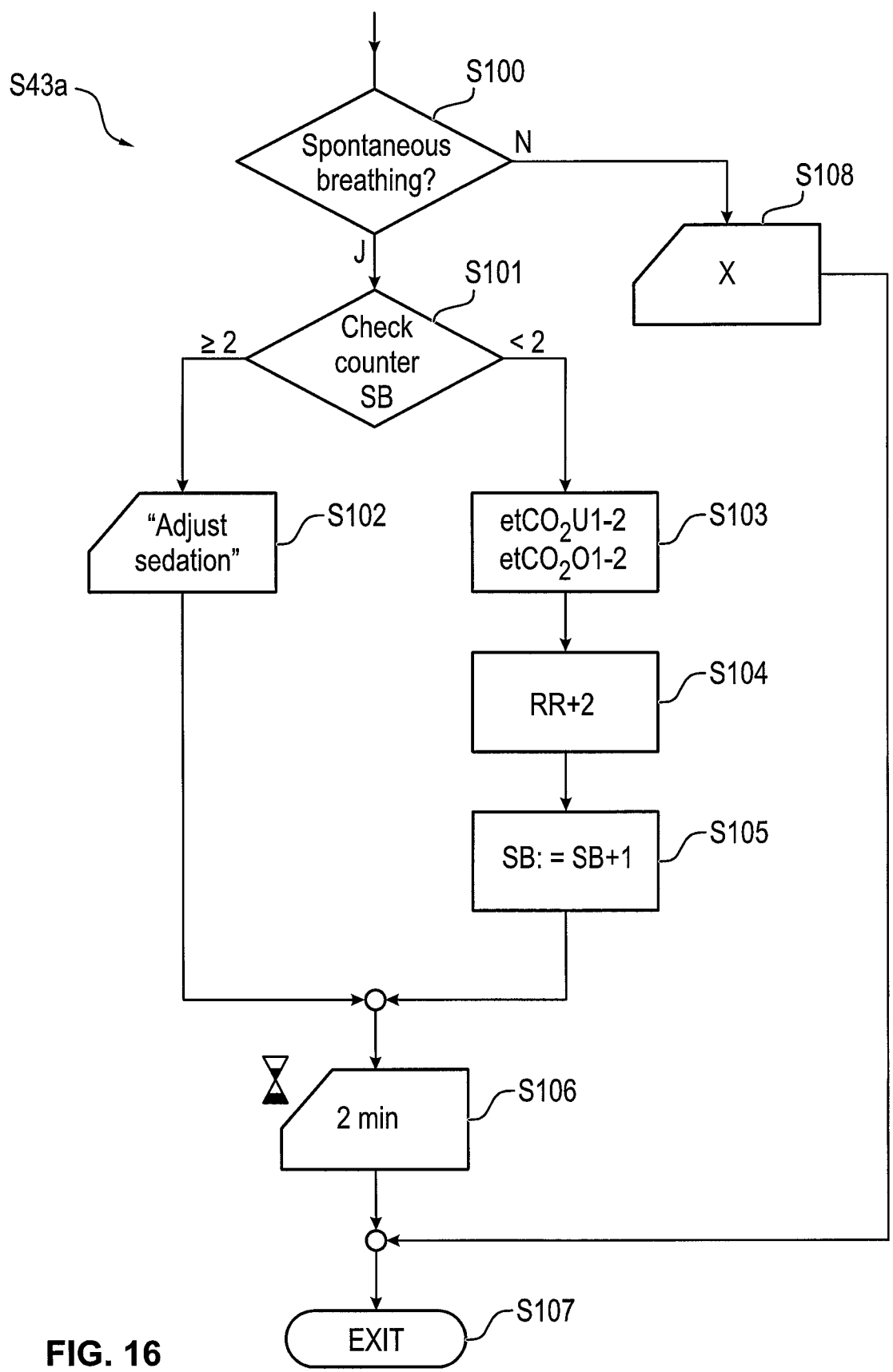
FIG. 16 is a flow diagram showing partial process steps for adapting concentration limit values.

It is explained now how an adaptation of the concentration limit values is preferably carried out in partial step S43a. FIG. 16 shows additional partial steps of partial step S43a of FIG. 7 for this.

FIG. 16 shows partial steps that disclose a partial process, in which spontaneous breathing activity of the patient is detected on the basis of the detected volume flow and wherein the carbon dioxide limit values are then adapted as a function of the detection result. The ventilation rate is preferably also adapted as a function of the detection result.

It is checked in the first partial step S100 whether a spontaneous breathing activity of the patient is present. The signal of the volume flow sensor is used for this, and it is inferred from the fact that this signal is exceeded over a trigger threshold, as was already explained before in reference to FIG. 1, that a spontaneous breath or a spontaneous breathing activity of the patient is present. Since a mode of the pressure control ventilation is involved in this exemplary embodiment, no provisions are made per se for the patient himself to have a spontaneous breathing activity. Such attempts at spontaneous breathing shall therefore be prevented and the pressure control ventilation shall be carried out such that the concentration limit values for the end-expiratory carbon dioxide concentration are adapted as a function of the detection results from partial step S100.

If no spontaneous breathing activity of the patient was detected in partial step S100, the process is branched off to partial process step S108, in which output of a warning "Adjust Sedation,", which possibly took place before, as is shown in partial step 102, is canceled. This is preferably carried out by means of an output signal AGS from FIG. 5. The device BV according to FIG. 5 preferably has for this a display unit AE for displaying the output signal AGS.

Partial step S107, which ends the partial process according to FIG. 16, will then take place.

If spontaneous breathing activity of the patient was detected in partial process step S100, the process is branched off further to partial process step S101. A counter SB, which was set to the value 0 before the beginning of the process according to the present invention, is checked here. If the counter is lower than a preset value, for example, the value 2, the process is branched off from the partial process step S101 to the partial process step S103. The concentration limit values etCO2U1 and etCO2O1 are then adapted in this partial process step S103. This is carried out consequently depending on whether a spontaneous breathing activity of the patient was detected in the partial step S100.

These carbon dioxide limit values in step 103 are preferably reduced by a preset value. This value is preferably the value 2.

Further, an adaptation of the ventilation rate RR is performed in a subsequent partial process step S104. This is preferably an increase in the ventilation rate RR by a preset value, preferably the value 2.

Further, the counter SB is then increased in the partial process step S105. The control value (2) of the counter SB represents a maximum number of attempts at adapting the concentration limit values etCO2U1, etCO2O2 and the ventilation rate RR, which are allowed to be used before the warning of step S102 is outputted. The warning of step S102 indicates the presence of detected attempts at spontaneous breathing by the patient.

After partial step S105, the process proceeds further to a partial process step S106, which lasts for a preset duration. This duration is preferably 2 minutes.

The process is then branched off further to the partial process step S107, which ends the partial process of step S43a of FIG. 7.

It is consequently seen that an adaptation of the concentration limit values etCO2U1 and etCO2O1 is only carried out in the partial process step S101 in the partial process step S103 if a maximum number of attempts at adapting the limit values and the ventilation rate (here: 2 attempts) have not yet been exhausted. Therefore, if the concentration limit values and the ventilation rate have already been adapted with the preset number of attempts at adaptation, the warning from step S102 is outputted in the partial process step S101. The process is then consequently branched off from step S101 to step S102, because the adaptation of the concentration limit values and of the ventilation rate have not possibly led to the desired effect.

An output is then made to the clinician in partial process step S102, and the clinician is prompted with this output to adapt the degree of sedation of the patient in order to prevent the spontaneous breathing activity of the patient.

Figure 9:
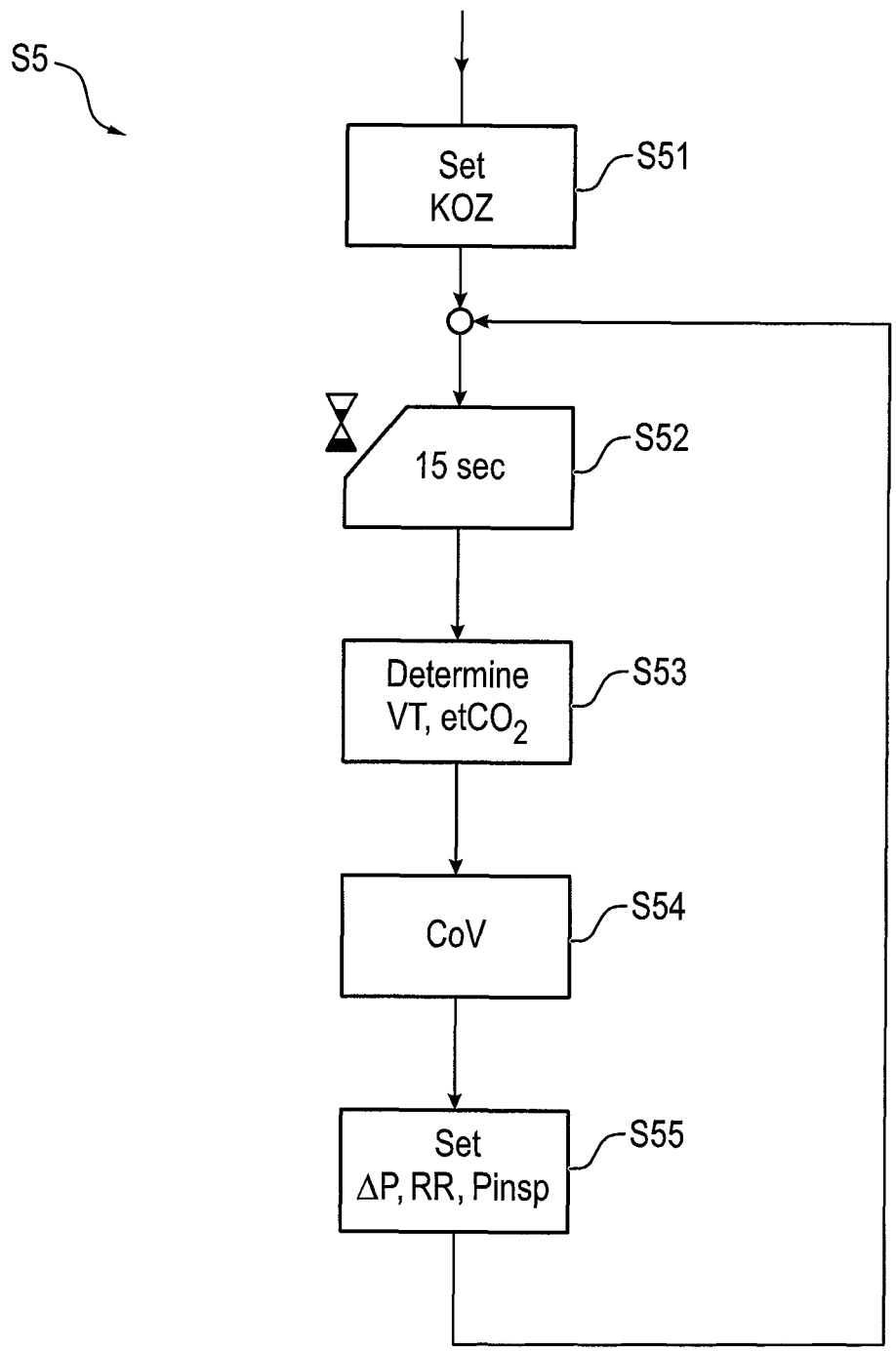
FIG. 9 is a flow diagram showing process steps according to a second embodiment of the process according to the present invention.

FIG. 9 shows partial process steps for carrying out the process according to the present invention according to the second embodiment. According to the first partial step S51, limit values are again initialized or defined. Taking the specifications concerning the lung properties ("Lung Mechanic") as well as a gas exchange rate or a degree of ventilation ("Level of Ventilation") from Tables T10 and T11 of FIG. 14 into account, corresponding first volume limit values VTU1, VTO2 as well as corresponding first concentration limit values etCO2U1, etCO2O1 can be determined for this from Table T3 of FIG. 12b. Using the data explained above with reference to FIG. 8, corresponding second volume limit values VTU2, VTO2 as well as corresponding second concentration limit values etCO2U2, etCO2O2 can, furthermore, be determined.

The process from FIG. 9 carries out a pressure control ventilation with spontaneous breathing activity of the patient permitted, as was explained before with reference to FIG. 3 and FIG. 1. Such a pressure control ventilation with spontaneous breathing activity permitted thus uses as the first desired pressure value the value ΔP as well as in conjunction with the minimum pressure PEEP, which is used during patient-triggered phases of inhalation based on spontaneous breathing, as well as a second desired pressure value Pinsp, which is used during phases of pressure control with triggering based on the preset ventilation rate. The rate RR is the ventilation rate here, which defines the time at which at least one pressure control ventilation of the patient is carried out at the latest and the rate at which it is carried out.

After initializing the limit values in partial step S51, there is at first a preset waiting period of preferably 15 sec in partial step S52.

The tidal volume VT as well as the end-expiratory carbon dioxide concentration etCO2, as was explained before with reference to FIG. 7 and partial step S43, are then determined within the framework of partial step S53.

Further, a classification of the ventilation relative to the tidal volume VT as well as to the end-expiratory carbon dioxide concentration value etCO2 is performed in partial step S54 as was explained before with reference to FIG. 7 and to partial step S44.

The adaptation of the two desired pressure values ΔP as well as Pinsp as well as of the ventilation rate RR is now performed within the framework of partial step S55. Using the results from partial step S54 and from Tables T10 and T11 of FIG. 14 on the basis of Table T20 of FIG. 15, a degree of change dP, which is applied to both the first desired pressure value ΔP and the second desired pressure value Pinsp, can be determined for this. Further, a degree of change dRR can be determined for the ventilation rate RR on the basis of Table T20 of FIG. 15. This degree of change dRR is then applied to the ventilation rate RR.

The process then returns to partial step S52.

Figure 10:
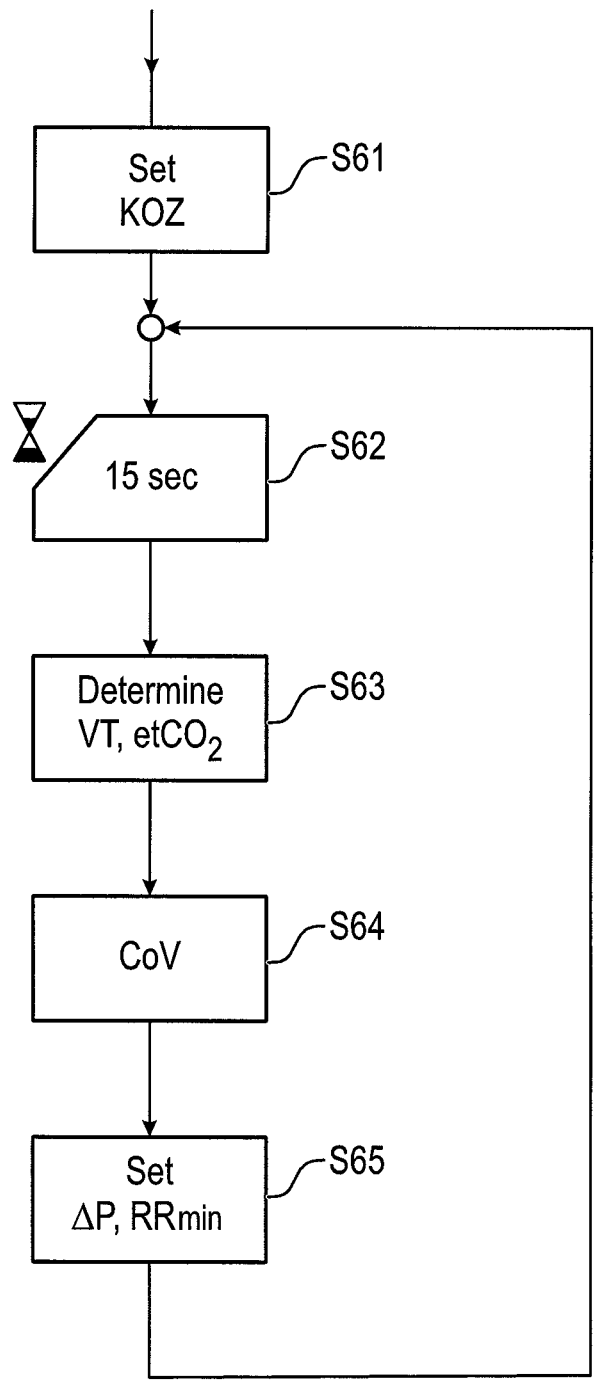
FIG. 10 is a flow diagram showing process steps according to a third embodiment of the process according to the present invention.

FIG. 10 shows the carrying out of the process according to the present invention according to the third embodiment. This is a ventilation with triggering based on spontaneous breathing activity for phases of inhalation with pressure support as was explained before with reference to FIG. 3 and FIG. 1. The value ΔP is used as the desired pressure value. The ventilation rate RRmin is not used here to actuate the breathing gas delivery unit by the computer, but only to determine whether the computer shall output a warning signal WS, as was described before.

The above-described limit values and the comfort zone are set in partial step S61, taking the specifications concerning the lung properties as well as the degree of ventilation and the gas exchange rate of the patient into consideration, as was explained before with reference to steps S41 and S51 of FIGS. 7 and 9, respectively. Table T4 of FIG. 13 is used for this.

There is a preset waiting period of preferably 15 sec in partial step S62.

As was explained before with reference to FIG. 7 and partial step S43 as well as partial step S53 of FIG. 9, the tidal volume VT as well as the end-expiratory carbon dioxide concentration etCO2 are then determined in partial step S63.

A classification of the ventilation in reference to the tidal volume VT as well as in reference to the end-expiratory carbon dioxide concentration etCO2, as was explained before with reference to the partial process steps S44 and S54 in FIGS. 7 and 9, respectively, is then carried out, in turn, in partial step S64. Depending on the results from partial step S64, a pressure change parameter dP as well as a rate change parameter dRR are then determined in partial step S65 and with the use of Table T20 of FIG. 15 as a function of the results from partial step S64. The desired pressure value ΔP is then changed by the pressure change parameter dP. The rate RRmin is then changed by the rate change parameter dRR.

The process then returns to step S62.

Figure 17:
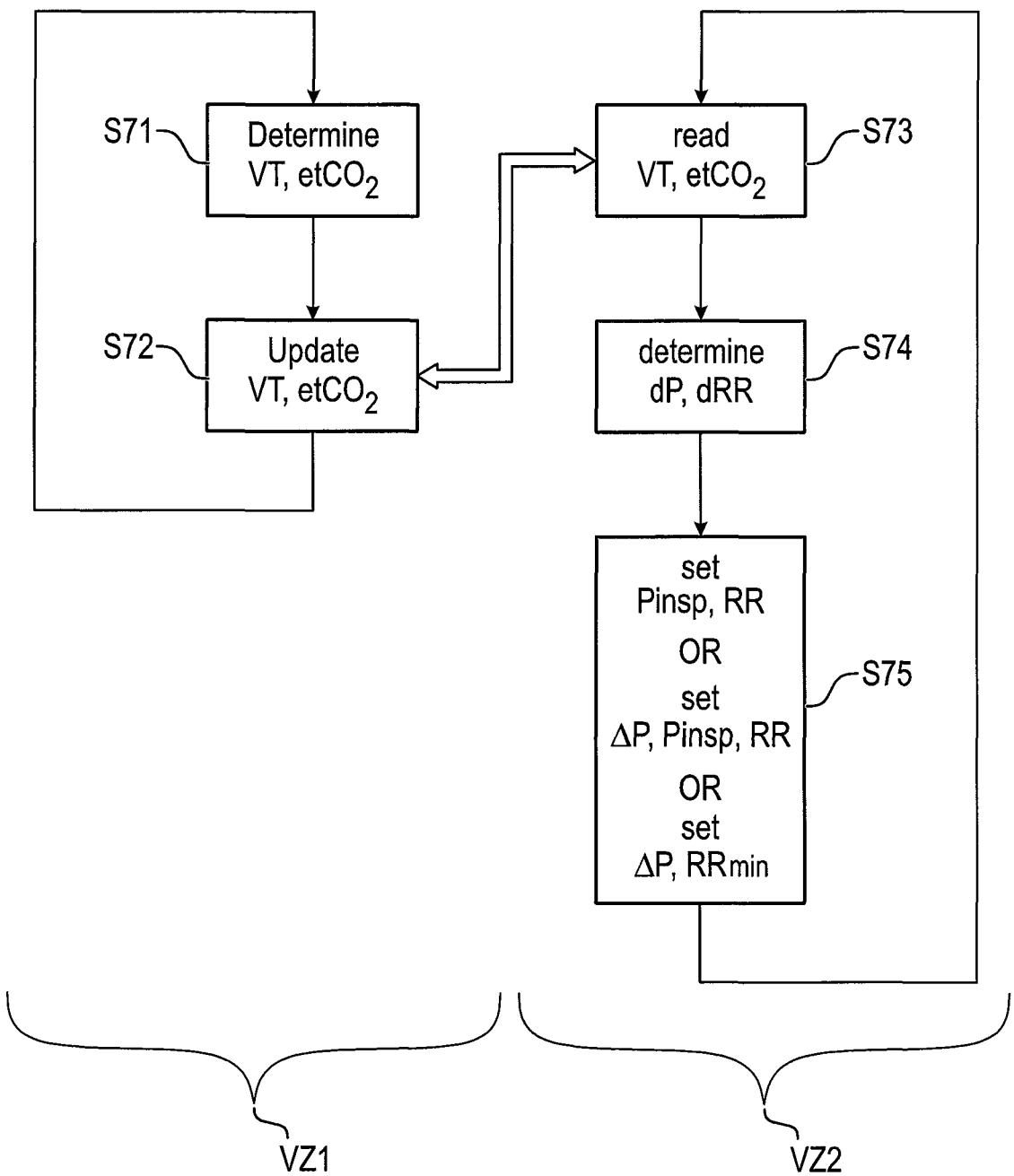
FIG. 17 is a flow diagram showing preferred alternative partial process steps for the case in which a target tidal volume and a target carbon dioxide concentration are taken into account.

FIG. 17 shows preferred alternative partial process steps for the case in which the adaptation of the desired pressure value, Pinsp and/or ΔP, and the adaptation of the ventilation rate, RR or RRmin, is performed as a function of the determined tidal volume, a target tidal volume, the determined end-expiratory carbon dioxide concentration and a target carbon dioxide concentration.

The change in the desired pressure value and in the ventilation rate, which is explained now in more detail on the basis of FIG. 17, can be carried out as an alternative to one of the three embodiments M1, M2 or M3 from FIG. 6, which were each explained on the basis of FIGS. 7, 9 and 10, respectively, and different parameters are adapted in step S75 depending on whether a pressure control ventilation with attempts at spontaneous breathing permitted or a purely pressure support ventilation with attempts at spontaneous breathing permitted or demanded is carried out.

The known parameters of the desired pressure value Pinsp and of the ventilation rate RR are adapted in step S75 in case of a purely pressure control ventilation as a function of the measured tidal volume VT and of the end-expiratory carbon dioxide concentration etCO2. The parameters of the desired pressure values Pinsp and ΔP as well as the ventilation rate RR are adapted in step S75 as a function of the measured tidal volume VT and of the end-expiratory carbon dioxide concentration etCO2 in case of pressure control ventilation with attempts at spontaneous breathing. In case of purely pressure support ventilation, the parameters of the desired pressure value ΔP and of the ventilation rate RRmin are adapted in step S75 as a function of the measured tidal volume VT and of the end-expiratory carbon dioxide concentration etCO2.

The steps S71 and S72 take place consecutively in a first process branch VZ1. A measured tidal volume VT and an end-expiratory carbon dioxide concentration etCO2 are determined in step S71 on the basis of the volume flow signal and of the carbon dioxide concentration signal.

The computer R according to FIG. 5 determines a tidal volume VT inhaled by the patient, preferably in mL, on the basis of the detected volume flow. The computer preferably determines for this the tidal volume as an integral value of the volume flow over this duration Ti on the basis of the detected volume flow and of a preset duration Ti of the inspiratory phase. As an alternative, a duration of an inspiratory phase can be determined such that when a volume flow threshold value FT is exceeded, the start of the inspiratory phase is inferred, and the end of the inspiratory phase is inferred when the volume flow threshold value FT is subsequently fallen below.

The computer further determines an end-expiratory carbon dioxide concentration etCO2, preferably in mmHg, on the basis of the detected carbon dioxide concentration. The end of an end-expiratory phase is then preferably inferred by comparison of the volume flow, as is shown in FIG. 1, and of a lower or negative USW threshold value when the detected volume flow passes through the lower threshold value from below.

The determined variables VT and etCO2 are then updated in process step S72. This is preferably carried out such that the computer R stores the determined variables VT and etCO2 in the memory MEM according to FIG. 5. It may be assumed, for example, that such an updating of the determined variables takes place every 1 to 4 sec, but the present invention is not limited to this value range.

In a process branch VZ2 taking place simultaneously with the process step VZ1, the determined variables VT and etCO2 are first read from the memory unit MEM according to FIG. 5.

A pressure change dP and a rate change RR are then determined in a process step S74. A target tidal volume VTZ of preferably VTZ=500 mL is preset now. Further, a target carbon dioxide concentration etCO2 of preferably etCO2=38 mmHg is preset. Further, a compliance CL of the patient's lungs preferably equaling CL=50 mL/mbar is preferably preset. An action coefficient DetCo2 of a change in the end-expiratory carbon dioxide concentration etCO2 on the change dRR of the ventilation rate is preferably preset as DetCo2=−6 mmHg/(1/minute).

The entirety of the three partial steps S73, S74 and S75 is preferably processed within a time of 10 msec (milliseconds), so that the pressure change dP and the rate change are applied every 10 msec to the desired pressure value and the ventilation rate, respectively.

The pressure change dP can then be determined according to $$dP = \frac{VTZ - VT}{CL} \cdot \frac{10^{-3} \text{ sec}}{120 \text{ sec}}$$

The rate change can then be determined according to $$dRR = \frac{etCO2Z - etCO2}{DetCO2} \cdot \frac{10^{-3} \text{ sec}}{120 \text{ sec}}$$

The respective rear correction term $$\frac{10^{-3} \text{ sec}}{120 \text{ sec}}$$

takes into consideration the fact that the variables dP and dRR are changed more rapidly in branch VZ2 than the measured tidal volume VT and the end-expiratory carbon dioxide concentration etCO2 in branch VZ1.

If a purely pressure control ventilation is carried out, the adaptation of the relevant parameters is carried out in step S75 according to Pinsp:=Pinsp+dP RR:=RR+dRR.

If a pressure control ventilation with attempts at spontaneous breathing is carried out, the adaptation of the relevant parameters is carried out in step S75 according to Pinsp:=Pinsp+dP ΔP:=ΔP+dP RR:=RR+dRR.

If a purely pressure support ventilation is carried out, the adaptation of the relevant parameters is carried out in step S75 according to ΔP:=ΔP+dP RRmin=RRmin+dRR.

Even though some aspects were described in connection with a device, it is obvious that these aspects also represent a description of the corresponding process, so that a block or a component of a device can also be defined as a corresponding process step or as a feature of a process step. Analogously hereto, aspects that were described in connection with a process step or as a process step also represent a description of a corresponding block/step or detail or feature of a corresponding device, and the device or the corresponding computer is configured to carry out the process step.

The computer R shown in FIG. 5 is to be considered to be at least one computer. An implementation of at least one computer R may also be embodied by a combination of a plurality of computers, preferably by the use of software in connection with hardware. Depending on certain implementation requirements, exemplary embodiments of the present invention may be implemented in hardware and/or in software. The implementation may be carried out with the use of a digital storage medium, for example, a floppy disk, a DVD, a Blu-Ray disk, a CD, a ROM, a PROM, an EPROM, an EERPROM or a FLASH memory, a hard drive or another magnetic or optical memory, on which electronically readable control signals, which can or do interact with a programmable hardware component such that the respective process is carried out, are stored.

A programmable hardware component may be formed by a processor, a computer processor (CPU=Central Processing Unit), a graphics processor (GPU=Graphics Processing Unit), a computer, a computer system, an application-specific integrated circuit (ASIC=Application-Specific Integrated Circuit), an integrated circuit (IC=Integrated Circuit), a System on Chip (SOC), a programmable logic component or a field-programmable gate array with a microprocessor (FPGA=Field Programmable Gate Array).

The digital storage medium may therefore be machine- or computer-readable. Some exemplary embodiments consequently comprise a data storage medium, which has electronically readable control signals, which are capable of interacting with a programmable computer system or with a programmable hardware component such that one of the processes being described here is carried out. An exemplary embodiment is consequently a data storage medium (or a digital storage medium or a computer-readable medium), on which the program for carrying out one of the processes being described here is recorded.

Exemplary embodiments of the present invention may generally be implemented as program, firmware, computer program or computer program product with a program code or as data, wherein the program code or the data act so as to carry out one of the processes when the program is running on a processor or on a programmable hardware component. The program code or the data may also be stored, for example, on a machine-readable medium or data storage medium. The program code or the data may occur, among other things, as source code, machine code or byte code as well as other intermediate code.

A further exemplary embodiment is, furthermore, a data stream, a signal sequence or a sequence of signals, which data stream or sequence represents the program for carrying out one of the processes described herein. The data stream, the signal sequence or the sequence of signals may be configured, for example, such as to be transferred via a data communication link, for example, via Internet or another network. Exemplary embodiments are thus also signal sequences representing data, which are suitable for transmission via a network or a data communication link, wherein the data represent the program.

A program according to an exemplary embodiment may implement one of the processes during its execution, for example, by reading storage locations or by writing a datum or a plurality of data into these, wherein switching operations or other operations are optionally brought about in transistor structures, in amplifier structures or in other electrical, optical, magnetic components or components operating according to another principle of action. Data, values, sensor values or other information can correspondingly be detected, determined or measured by reading a storage location. A program can therefore detect, determine or measure variables, values, measured variables and other information by reading one or more storage locations as well as bring about, prompt or carry out an action as well as actuate other devices, machines and components by writing to one or more storage locations.

While specific embodiments of the invention have been shown and described in detail to illustrate the application of the principles of the invention, it will be understood that the invention may be embodied otherwise without departing from such principles.

The invention claimed is:

1. A ventilator for an automated ventilation of a patient, the ventilator comprising:
    an expiratory port and an inspiratory port for connecting a ventilation tube for supplying a breathing gas to a patient;
    a breathing gas delivery unit;
    at least one volume flow sensor for detecting a volume flow of the breathing gas;
    at least one breathing gas sensor for detecting a carbon dioxide concentration in the breathing gas;
    at least one pressure sensor for detecting a pressure of the breathing gas; and
    at least one computer, wherein the at least one computer is configured:
    to actuate the breathing gas delivery unit as a function of the detected pressure and of a preset desired pressure value;
    to perform an adaptation of the desired pressure value as a function of the detected volume flow and as a function of the detected carbon dioxide concentration;
    to perform an adaptation of a ventilation rate as a function of the detected volume flow and as a function of the detected carbon dioxide concentration;
    to determine a tidal volume fed to the patient on the basis of the detected volume flow;
    to determine an end-expiratory carbon dioxide concentration on the basis of the detected carbon dioxide concentration;
    to perform the adaptation of the desired pressure value and the adaptation of the ventilation rate as a function of the determined tidal volume and of the determined end-expiratory carbon dioxide concentration; and
    to perform the adaptation of the desired pressure value and the adaptation of the ventilation rate as a function of:
    the determined tidal volume;
    an upper volume limit value;
    a lower volume limit value;
    the determined end-expiratory carbon dioxide concentration;
    an upper carbon dioxide limit value; and
    a lower concentration limit value, wherein the at least one computer is further configured:
    to actuate the breathing gas delivery unit as a function of the detected pressure, of the preset desired pressure value and further of the ventilation rate;
    to actuate the breathing gas delivery unit such that the automated ventilation is carried out as a pressure control ventilation;
    to detect a spontaneous breathing activity of the patient on the basis of the detected volume flow; and
    to adapt concentration limit values as a function of the detection result of the spontaneous breathing activity of the patient.

2. The ventilator in accordance with claim 1, wherein the at least one computer is further configured:
    to actuate the breathing gas delivery unit such that the automated ventilation is carried out as a pressure support ventilation; and
    to control an output of a warning signal as a function of the ventilation rate.

3. The ventilator in accordance with claim 1, wherein the at least one computer is further configured to perform the adaptation of the desired pressure value and the adaptation of the ventilation rate as a function of a target tidal volume and of a target carbon dioxide concentration.

4. The ventilator in accordance with claim 1, wherein the at least one computer is configured to select
    the upper volume limit value;
    the lower volume limit value;
    the upper carbon dioxide limit value; and
    the lower concentration limit value
as a function of a specification concerning a lung property of the patient.

5. The ventilator in accordance with claim 1, wherein the at least one computer is further configured to select
    the upper carbon dioxide limit value; and
    the lower concentration limit value
as a function of a specification concerning a desired gas exchange rate of the patient.

6. The ventilator in accordance with claim 1, wherein:
    the upper volume limit value is a first upper volume limit value;
    the lower volume limit value is a first lower volume limit value;
    the at least one computer is further configured to perform the adaptation of the desired pressure value and the adaptation of the ventilation rate as a function of:
    a second upper volume limit value; and
    a second lower volume limit value.

7. The ventilator in accordance with claim 1, wherein:
    the carbon dioxide limit value is a first upper concentration limit value;
    the lower concentration limit value is a first lower concentration limit value; and
    the at least one computer is further configured to perform the adaptation of the desired pressure value and the adaptation of the ventilation rate as a function of:
    a second upper concentration limit value; and
    a second lower concentration limit value.

8. The ventilator in accordance with claim 1, wherein the ventilation rate corresponds to a number of breaths per a unit of time.

9. A process for an automated ventilation of a patient, the process comprising the steps of:
    feeding a breathing gas to a patient via an inspiratory port and return of the breathing gas via an expiratory port by operating a breathing gas delivery unit;
    detecting a volume flow of the breathing gas by means of at least one volume flow sensor;
    detecting a carbon dioxide concentration in the breathing gas by means of at least one breathing gas sensor;
    detecting a pressure of the breathing gas by means of at least one pressure sensor;
    actuating the breathing gas delivery unit as a function of the detected pressure and of a preset desired pressure value by means of at least one computer, wherein:
    the desired pressure value is adapted as a function of the detected volume flow and as a function of the detected carbon dioxide concentration;
    a ventilation rate is adapted as a function of the detected volume flow and as a function of the detected carbon dioxide concentration by means of the at least one computer;
    a tidal volume fed to the patient is determined on the basis of the detected volume flow;
    an end-expiratory carbon dioxide concentration is determined on the basis of the detected carbon dioxide concentration;

adaptation of the desired pressure value and the adaptation of the ventilation rate are performed as a function of the determined tidal volume and of the determined end-expiratory carbon dioxide concentration; and the adaptation of the desired pressure value and the adaptation of the ventilation rate is performed as a function of:

the determined tidal volume;
an upper volume limit value;
a lower volume limit value;
the determined end-expiratory carbon dioxide concentration;
an upper carbon dioxide limit value; and
a lower concentration limit value, wherein the at least one computer is configured:
to actuate the breathing gas delivery unit as a function of the detected pressure, of the preset desired pressure value and further of the ventilation rate;
to actuate the breathing gas delivery unit such that the automated ventilation is carried out as a pressure control ventilation;
to detect a spontaneous breathing activity of the patient on the basis of the detected volume flow; and
to adapt concentration limit values as a function of the detection result of the spontaneous breathing activity of the patient.

10. The process in accordance with claim 9, wherein the ventilation rate corresponds to a number of breaths per a unit of time.

11. A computer device for a ventilator for an automated ventilation of a patient, the computer device comprising a computer, wherein the computer is configured to:
detect a volume flow signal, which indicates a volume flow of a breathing gas;
detect a carbon dioxide concentration signal, which indicates a carbon dioxide concentration in the breathing gas;
detect a pressure signal, which indicates a pressure of the breathing gas;
provide an actuating signal for a breathing gas delivery unit, wherein the computer is configured to determine the actuating signal as a function of the detected pressure signal and of a preset desired pressure value;
perform an adaptation of the desired pressure value as a function of the detected volume flow and as a function of the detected carbon dioxide concentration;
perform an adaptation of a ventilation rate as a function of the detected volume flow and as a function of the detected carbon dioxide concentration;
determine a tidal volume fed to the patient on the basis of the detected volume flow;
determine an end-expiratory carbon dioxide concentration on the basis of the detected carbon dioxide concentration;
perform the adaptation of the desired pressure value and the adaptation of the ventilation rate as a function of the determined tidal volume and of the determined end-expiratory carbon dioxide concentration;
actuate the breathing gas delivery unit as a function of the detected pressure, of the preset desired pressure value and further of the ventilation rate;
actuate the breathing gas delivery unit such that the automated ventilation is carried out as a pressure control ventilation;
detect a spontaneous breathing activity of the patient on the basis of the detected volume flow;
adapt concentration limit values as a function of the detection result of the spontaneous breathing activity of the patient; and
perform the adaptation of the desired pressure value and the adaptation of the ventilation rate as a function of:
the determined tidal volume;
an upper volume limit value;
a lower volume limit value;
the determined end-expiratory carbon dioxide concentration;
an upper carbon dioxide limit value; and
a lower concentration limit value.

12. The computer device in accordance with claim 11, wherein the ventilation rate corresponds to a number of breaths per a unit of time.

13. A process for operating a ventilator for an automated ventilation of a patient, the process comprising the steps of:
detecting a volume flow signal, which indicates a volume flow of a breathing gas, and detecting a carbon dioxide concentration signal, which indicates a carbon dioxide concentration in the breathing gas;
detecting a pressure signal, which indicates a pressure of the breathing gas;
providing an actuating signal for a breathing gas delivery unit as a function of the detected pressure signal and of a preset desired pressure value;
adapting the desired pressure value as a function of the detected volume flow and as a function of the detected carbon dioxide concentration;
adapting a ventilation rate as a function of the detected volume flow and as a function of the detected carbon dioxide concentration;
determining a tidal volume fed to the patient on the basis of the detected volume flow;
determining an end-expiratory carbon dioxide concentration on the basis of the detected carbon dioxide concentration; and
performing the adaptation of the desired pressure value and the adaptation of the ventilation rate as a function of the determined tidal volume and of the determined end-expiratory carbon dioxide concentration;
actuating the breathing gas delivery unit as a function of the detected pressure, of the preset desired pressure value and the ventilation rate;
actuating the breathing gas delivery unit such that the automated ventilation is carried out as a pressure control ventilation;
detecting a spontaneous breathing activity of the patient on the basis of the detected volume flow;
adapting concentration limit values as a function of the detected spontaneous breathing activity of the patient; and
performing the adaptation of the desired pressure value and the adaptation of the ventilation rate as a function of:
the determined tidal volume;
an upper volume limit value;
a lower volume limit value;
he determined end-expiratory carbon dioxide concentration;
an upper carbon dioxide limit value; and
a lower concentration limit value.

14. The process in accordance with claim 13, wherein the process is carried out with a computer program on at least one computer.

15. The process in accordance with claim 13, wherein the process is executed with a program with a program code on a computer, on a processor or on a programmable hardware component.

16. The process in accordance with claim 13, wherein the ventilation rate corresponds to a number of breaths per a unit of time.

* * * * *